(12) United States Patent
Lynch et al.

(10) Patent No.: US 8,173,710 B2
(45) Date of Patent: May 8, 2012

(54) BICYCLIC SPHINGOSINE 1-PHOSPHATE ANALOGS

(75) Inventors: Kevin R. Lynch, Charlottesville, VA (US); Timothy L. MacDonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 12/978,087

(22) Filed: Dec. 23, 2010

(65) Prior Publication Data

US 2011/0195936 A1    Aug. 11, 2011

Related U.S. Application Data

(63) Continuation of application No. 12/189,010, filed on Aug. 8, 2008, which is a continuation of application No. PCT/US2007/003645, filed on Feb. 9, 2007.

(60) Provisional application No. 60/771,789, filed on Feb. 9, 2006, provisional application No. 60/855,960, filed on Nov. 1, 2006, provisional application No. 60/860,694, filed on Nov. 21, 2006.

(51) Int. Cl.
    *A61K 31/135* (2006.01)
    *C07C 211/30* (2006.01)
(52) U.S. Cl. ......................................... 514/657; 564/428
(58) Field of Classification Search .................. 514/364, 514/533; 548/131; 560/54
See application file for complete search history.

(56) References Cited

U.S. PATENT DOCUMENTS

| | | | |
|---|---|---|---|
| 3,153,092 A | 10/1964 | Burger | |
| 4,939,130 A | 7/1990 | Jaeggi et al. | |
| 5,405,988 A | 4/1995 | Klar et al. | |
| 6,069,251 A | 5/2000 | Thurkauf et al. | |
| 6,875,757 B2 | 4/2005 | Miller et al. | |
| 7,060,697 B2 | 6/2006 | Marsilje et al. | |
| 7,064,217 B2 | 6/2006 | MacDonald et al. | |
| 7,241,790 B2 | 7/2007 | Lynch et al. | |
| 2004/0224941 A1 | 11/2004 | Seko et al. | |
| 2005/0023386 A1 | 2/2005 | Haskell | |
| 2005/0032744 A1 | 2/2005 | Michaelis et al. | |
| 2006/0122181 A1 | 6/2006 | Ikemoto et al. | |
| 2006/0135786 A1 | 6/2006 | Saha et al. | |
| 2006/0211656 A1 | 9/2006 | Albert et al. | |
| 2006/0223866 A1 | 10/2006 | Evindar et al. | |
| 2007/0088002 A1 | 4/2007 | Lynch et al. | |
| 2007/0191313 A1 | 8/2007 | Beard et al. | |
| 2008/0249070 A1 | 10/2008 | Lynch et al. | |
| 2009/0042955 A1* | 2/2009 | Lynch et al. | 514/364 |
| 2009/0062238 A1 | 3/2009 | Lynch et al. | |
| 2009/0105315 A1 | 4/2009 | Lynch et al. | |
| 2009/0137531 A1 | 5/2009 | Lynch et al. | |
| 2009/0253759 A1 | 10/2009 | Lynch et al. | |
| 2009/0253760 A1 | 10/2009 | Lynch et al. | |
| 2009/0253761 A1 | 10/2009 | Lynch et al. | |
| 2010/0240617 A1* | 9/2010 | Lynch et al. | 514/143 |

FOREIGN PATENT DOCUMENTS

| | | |
|---|---|---|
| DE | 1056139 B | 4/1959 |
| DE | 3544373 A1 | 6/1987 |
| EP | 1553091 A1 | 7/2005 |
| EP | 1602660 A1 | 12/2005 |
| GB | 950388 A | 2/1964 |
| JP | 1994135935 | 5/1994 |
| JP | 1994135936 | 5/1994 |
| JP | 2002316985 | 10/2002 |
| JP | 2004307442 | 4/2004 |
| WO | WO-9935259 A1 | 7/1999 |
| WO | WO-0160819 A1 | 8/2001 |
| WO | WO-0171022 A2 | 9/2001 |
| WO | WO-02076995 A2 | 10/2002 |
| WO | WO-02092068 A1 | 11/2002 |
| WO | WO-03059880 A1 | 7/2003 |
| WO | WO-03061567 A2 | 7/2003 |
| WO | WO-2004010987 A2 | 2/2004 |
| WO | WO-2004017917 A2 | 3/2004 |
| WO | WO-2004024673 A1 | 3/2004 |
| WO | WO-2004028521 A2 | 4/2004 |
| WO | WO-2004047743 A1 | 6/2004 |
| WO | WO-2004047743 A2 | 6/2004 |
| WO | WO-2004096752 A1 | 11/2004 |
| WO | WO-2004096757 A1 | 11/2004 |
| WO | WO-2004103279 A2 | 12/2004 |
| WO | WO-2004103306 A2 | 12/2004 |
| WO | WO-2005032465 A2 | 4/2005 |
| WO | WO-2005118523 A1 | 12/2005 |
| WO | WO-2006001463 A1 | 1/2006 |
| WO | WO-2006020951 A1 | 2/2006 |
| WO | WO-2007085451 A2 | 8/2007 |
| WO | WO-2007086001 A2 | 8/2007 |
| WO | WO-2007091396 A1 | 8/2007 |
| WO | WO-2007092638 A1 | 8/2007 |

(Continued)

OTHER PUBLICATIONS

"(3-benzoylamino-3-phenylcarbamoyl-propyl)-phophonic acid diethyl ester", Beilstein Registry No. 6240345, XP-0023802076, 1985.
"U.S. Appl. No. 12/189,010, Examiner Interview Summary mailed Nov. 23, 2010", 3 pgs.
"U.S. Appl. No. 12/189,010, Non Final Office Action mailed Jun. 23, 2010", 19 pgs.
"U.S. Appl. No. 12/189,010, Non Final Office Action mailed Dec. 27, 2010", 13 pgs.
"U.S. Appl. No. 12/189,010, Preliminary Amendment mailed Oct. 27, 2008", 3 pgs.
"U.S. Appl. No. 12/189,010, Response filed Mar. 4, 2010 to Restriction Requirement mailed Feb. 4, 2010", 3 pgs.

(Continued)

*Primary Examiner* — Kamal Saeed
*Assistant Examiner* — Kristin Bianchi
(74) *Attorney, Agent, or Firm* — Schwegman, Lundberg & Woessner, P.A.

(57) ABSTRACT

Compounds that have agonist activity at one or more of the S1P receptors are provided. The compounds are sphingosine analogs that, after phosphorylation, can behave as agonists at S1P receptors.

20 Claims, 11 Drawing Sheets

FOREIGN PATENT DOCUMENTS

| | | |
|---|---|---|
| WO | WO-2008079382 A1 | 7/2008 |
| WO | WO-2009023854 A1 | 2/2009 |
| WO | WO-2009043013 A2 | 4/2009 |
| WO | WO-2009146112 A2 | 12/2009 |

OTHER PUBLICATIONS

"U.S. Appl. No. 12/189,010, Response filed May 12, 2010 to Restriction Requirement Apr. 12, 2010", 3 pgs.

"U.S. Appl. No. 12/189,010, Restriction Requirement mailed Feb. 4, 2010", 11 pgs.

"U.S. Appl. No. 12/189,010, Restriction Requirement mailed Apr. 12, 2010", 3 pgs.

"Australian Application Serial No. 2007212193, Non Final Office Action dated Aug. 15, 2011", 2 pgs.

"European Application Serial No. 07763449.1, Office Action mailed Feb. 3, 2009", 4 pgs.

"European Application Serial No. 07763449.1, Office Action mailed Oct. 5, 2011", 4 pgs.

"European Application Serial No. 07763449.1, Office Action mailed Nov. 4, 2010", 5 pgs.

"European Application Serial No. 07763449.1, Response filed Feb. 22, 2011 to Office Action mailed Nov. 4, 2010", 9 pgs.

"International Application Serial No. PCT/US2007/003645, International Preliminary Report on Patentability mailed Aug. 12, 2008", 9 pgs.

"International Application Serial No. PCT/US2007/003645, International Search Report Jul. 16, 2007", 6 pgs.

"International Application Serial No. PCT/US2007/003645, Written Opinion mailed Aug. 9, 2008", 8 pgs.

"New Zealand Application Serial No. 570229, Examiner Report mailed Mar. 30, 2010", 2 pgs.

"New Zealand Application Serial No. 570229, Response filed Jun. 156, 2011 to Examiner Report mailed Mar. 30, 2010", 19 pgs.

"New Zealand Application Serial No. 570229, Subsequent Examiner Report mailed Jul. 8, 2011", 2 pgs.

Bandini, M, et al., "An Effective and Useful Synthesis of Enantiomerically Enriched Arylglycinols", European Journal of Organic Chemistry, 10, (May, 2001), 1937-1942.

Bertus, P, et al., "New and easy route to primary cyclopropylamines from nitriles", Chem Commun, DOI: 10.1039/b105293b, (2001), 1792-1793.

Brinkmann, Voker, et al., "The Immune Modulator FTY720 Targets Sphingosine 1-Phosphate Receptors", J Biol Chem 277, (2002), 21453-21457.

Brinkmann, Volker, et al., "FTY720: Altered Lymphocyte Traffic Results in Allograft Protection", Transplantation 72, (2001), 764-769.

Burger, A, et al., "1-Methyl-2-phenylcyclopropylamine", Journal of Medicine and Pharmaceutical Chemistry, vol. 4 No. 3, (1961), 4 pgs.

Chiba, K, et al., "FTY720, a Novel Immunosuppressant, Induces Sequestration of Circulating Mature Lymphocytes by Acceleration of Lymphocyte Homing in Rats. I. FTY720 Selectively Decreases the number of Circulating Mature Lymphocytes by Accelerating of Lymphocycte Homing", J Immunol 160, (1998), 5037-5044.

Choi, D, et al., "Synthesis and Anticonvulsant Activities of N-Benzyl-2-acetamidopropionamide Derivatives", J Med Chem 39, (1996), 1907-1916.

Clair, T, et al., "Autotaxin Hydrolyzes Sphingosylphosphorylcholine to Produce the Regulator of Migration, Sphingosine-1-Phosphate", Cancer Res 63, (2003), 5446-5453.

Clemens, J, et al., "Synthesis of 4(5)-Phenylimidazole-based analogues of sphingosine-1-phosphate and FTY720: Discovery of potent S1P1 receptor agonists", Bioorg & Med Chem Lett, (2005), 3568-3572.

Clemens, J, et al., "Synthesis of benzimidazole based analogues of sphingosine-1-phosphate: discovery of potent, subtype-selective S1P4 receptor agonists", Bioorg & Med Chem Letter, (2004), 4903-4906.

Clemens, J, et al., "Synthesis of Para-Alkyl Aryl Amide Analogues of Sphingosine-1-phosphate: Discovery of Potent S1P Receptor Agonists", Bioorg Med Chem Lett, (2003), 3401-3404.

Crosignani, S., et al., "4-Naphthyl-substituted bis(oxazoline): A new, easily recoverable and efficient chiral ligand in asymmetric catalysis of the Diels-Alder reaction", Tetrahedron, 54(51), (Dec. 17, 1998), 15721-15730.

Davis, M, et al., "Sphingosine 1-Phosphate Analogs as Receptor Antagonists", The J. of Bio Chem 280(11), (2005), 9833-9841.

Dworkin, R.H., "Advances in Neuropathic Pain: Diagnosis, Mechanisms, and Treatment Recommendations", Arch. Neurol, 60, (2003), 1524-1534.

Forrest, M, et al., "Immune Cell Regulation and Cardiovascular Effects of Sphingosine 1-Phosphate Receptor Agonists in Rodents are Mediated via Distinct Receptor Subtypes", J Pharmacol Exp Ther 309, (2004), 758-768.

Foss, F, et al., "Synthesis and biological evaluation of y-aminophosphonates as potent, subtype-selective sphingosine 1-phosphate receptor agonists and antagonists", Bioorganic & Medicinal Chemistry 15, (2007), 663-677.

Foss, F, et al., "Synthesis, stability and implications of phosphothioate agonists of sphingosine-1-phosphate receptors", Bioorganic & Medicinal Chemistry 15, (2005), 4470-4474.

Fujino, M, et al., "Amelioration of Experimental Autoimmune Encephalomyelitis in Lewis Rats by FTY720 Treatment", J Pharmacol Exp Ther 305, (2003), 70-77.

Graler, M.H., et al., "The immunosuppressant FTY720 down-regulates sphingosine 1-phosphate G-protein-coupled receptors", FASEB 18, (2004), 551-553.

Hale, J.J., et al., "A Rational Utilization of High-Throughput Screening Affords Selective, Orally Bioavailable 1-Benzyl-3-carboxyazetidine Sphingosine-1-phosphate-1 Receptor Agonists", Bioorg & Med Chem Lett 47, (2004), 6662-6665.

Hale, J.J., et al., "Potent S1P receptor agonist replicate the pharmacologic actions of the novel immune modulator FTY720", Bioorganic & Medicinal Chemistry Letters 14, (2004), 3351-3355.

Hale, J.J., et al., "Selecting against S1p3 enhances the acute cardiovascular tolerability of 3-(N-Benzyl)aminopropylphosphonic acid S1P receptor agonists", Bioorg & Med Chem Lett 14, (2004), 3501-3505.

Hale, J.J., et al., "The discovery of 3-(N-alkyl)aminopropylphosphonic acids as potent S1P receptor agonists", Bioorg & Med Chem Lett 14, (2004), 3495-3499.

Hanessian, S, et al., "Constrained azacyclic analogues of the immunomodulatory agent FTY720 as molecular probes for sphingosine 1-phosphate receptors", Bioorganic & Medicinal Chemistry Letters 17, (2007), 491-494.

Hoshino, Y, et al., "FTY720, a Novel Immunosupressant, Shows a Synergistic Effect in Combination With FK 506 in Rat Allograft Models", Transplant Proc 31, (1999), 1224-1226.

Im, Dong-Soon, et al., "Characterization fo a Novel Sphingosine 1-Phosphate Receptor, Edg-8", J. Biol Chem 275, (2000), 14281-14286.

Im, Dong-Soon, et al., "Characterization of the Human and Mouse Sphingosine 1-Phosphate Receptor, SIP5 (Edg-8): Structure-Activity Relationship of Sphingosine 1-Phosphate Receptors", Biochemistry 40, (2001), 14053-14060.

Jones, Leroy, et al., "Rapid Solution and Solid Phase Syntheses of Oligo(1,4-phenylene enthynylene)s with Thioester Termini: Molecular Scale Wires with Alligator Clips. Derivation of Iterative Reaction Efficiencies on a Polymer Support", J Org Chem 62, (1997), 1388-1410.

Kaiser, C, et al., "2-Substituted Cyclopropylamines, 1. Derivatives and Analogs of 2-Phenylcyclopropylamine", XP009032189, (Nov. 1962), 1243-1265.

Kawasaki, K, et al., "Enantioselective allylic oxidation of cycloalkenes by using Cu(II)-tris(oxazoline) complex as a catalyst", Tetrahedron, 53(18), (May 5, 1997), 6337-6350.

Kharel, Y, et al., "Sphingosine Kinase 2 Is Required for Modulation of Lymphocyte Traffic by FTY720", J Bio Chem vol. 280 No. 44, (Nov. 4, 2005), 36865-36872.

Kimura, T, et al., "High-Density Lipoprotein Stimulates Endothelial Cell Migration and Survival Through Sphingosine 1-Phosphate and Its Receptors", Arterioscler Thromb Vasc Biol 23, (2003), 1283-1288.

Kiuchi, Masatoshi, et al., "Synthesis and Immunosuppressive Activity of 2-Substituted 2-Aminopropane-1,3-diols and 2-Aminoethanols", J Med Chem 43, (2000), 2946-2961.

Kon, J, et al., "Comparison of Intrinsic Activities of the Putative Sphingosine 1-Phosphate Receptor Subtytpes to Regulate Several Signaling Pathways in Their cDNA-transfected Chines Hamter Ovary Cells", J Biol Chem 274, (1999), 23940-23947.

Kotera, et al., "Stereochemistry of aziridine formation by reduction of oximes with lithium aluminum hydride on aralkyl alkyl ketoximes and their tosylates", Chem Abst Registry Record 19352-04-6, 1968.

Lee, Menq-Jer, et al., "Sphingosine-1-Phosphate as a Ligand for the G Protein-Coupled Receptor EDG-1", Science 279, (1998), 1552-1555.

Lew, M, et al., "Analysis of Competitive agonist interactions by nonlinear regression", Trend Phamacol Sci 16, (1995), 328-337.

Li, Z, et al., "Discovery of Potent 3,5-Diphenyl-1,2,4,oxadiazole Sphingosine-1-phosphate-1 (S1P1) Receptor Agonists with Exceptional Selectivity against S1P2 and S1P3", Journal of Medicinal Chemistry vol. 48 No. 20, (Oct. 6, 2005), 6169-6173.

Maki, T, et al., "Prevention and Cure of Autoimmune Diabetes in Nonobese Diabetic Mice by Continuous Administration of FTY720", Transplantation 79, (2005), 1051-1055.

Maki, T, et al., "Prevention of Autoimmune Diabetes by FTY720 in Nonobese Diabetic Mice", Transplantation 74, (2002), 1684-1686.

Mandala, S, et al., "Alteration of Lymphocyte Trafficking by Sphingosine 1-Phosphate Receptor Agonists", Science 296, (2002), 346-349.

Matloubian, M, et al., "Lymphocyte egress from thymus and peripheral lymphoid organs is dependent on S1P receptor 1", Nature 427, (2004), 355-360.

Sanchez, T, et al., "Phosphorylation and Action of the Immunomodulator FTY720 Inhibits Vascular Endothelial Cell Growth Factor-Induced Vascular Permeability", J Biol Chem 278, (2003), 47281-47290.

Sanna, M.G., et al., "Enhancement of Capillary Leakage and Restoration of Lymphocyte Egress ba a Chiral S1P1 Antagonist in vivo", Nature Chemical Biology vol. 2, (Aug. 2006), 434-441.

Sanna, M.G., et al., "Sphingosine 1-Phosphate (S1P) Receptor Subtypes S1P1 and S1P3, Respectively, Regulate Lymphocyte Recirculation and Heart Rate", J Biol Chem 279, (2004), 13839-13848.

Suzuki, S, et al., "Immunosuppressive effect of a new drug, FTY720 on lymphocyte responses in vitro and cardiac allograft survival in rats", Transpl Immunol 4, (1996), 252-255.

Van Brocklyn, J.R., et al., "Sphingosine 1-Phosphate-induced Cell Rounding and Neurite Retraction Are Mediated by the G Protein-coupled Receptor H218", J Biol Chem 274, (1999), 4626-4632.

Vogler, R, et al., "Sphingosine-1-Phosphate and Its Potentially Paradoxical Effects on Critical Parameters of Cutaneous Wound Healing", No. 20, (2005), 6169-6173.

Xie, J.H., et al., "Sphingosine-1-Phosphate Receptor Agonism Impairs the Efficiency of the Loal Immune Response by Altering Trafficking of Naive and Antigen-Activated CD4+ T Cells", J Immunol 170, (2003), 3662-3670.

Yan, Lin, et al., "SAR studies of 3-arylpropionic acids as potent and selective agonists of sphingosine-1-phosphate receptor-1 (S1P1) with enhanced pharmacokinetic properties", Bioorganic & Medicinal Chemistry Letters, 17(3), (Feb. 1, 2007), 828-831.

Yanagawa, Y, et al., "FTY720, a Novel Immunosuppressant, Prolongs Rat Skin Allograft Survival by Decreasing T-Cell Infiltration into Graphs", Transplant Proc 31, (1999), 1227-1229.

Yanagawa, Y, et al., "The significance of timing of FTY720 administration on the immunosuppressive effect to prolong rat skin allograft survival", Int J Immunopharmacol 22, (2000), 597-602.

Yang, Z, et al., "The immune modulator FYT720 prevents autoimmune diabetes in nonobese diabetic mice", Clin Immunol 107, (2003), 30-35.

Zhang, T, et al., "Concurrent Overexpression of Cyclin D1 and Cyclin-dependent Kinase 4 (Cdk4) in Intestinal Adenomas from Multiple Intestinal Neoplasia (Min) Mice and Human Familial Adenomatous Polyposis Patients", Cancer Res 57, (1997), 169-175.

Zhang, Y.H., et al., "Intracellular sphingosine 1-phosphate mediates the increased excitability produced by nerve growth factors in rat sensory neurons", J physiol 575, (2006), 101-113.

Zhang, Y.H., et al., "Sphingosine-1-Phosphate Via Activation of a G-Protein-Coupled Receptor(s) Enhances the Excitability of Rat Sensory Neurons", J. Neurophysiol 96, (2006), 1042-1052.

* cited by examiner

FTY720

AAL151

XXVI

XXVII

XXVIII

XXIX

SCHEME 3

BICYCLIC SPHINGOSINE 1-PHOSPHATE ANALOGS

CROSS-REFERENCE TO RELATED APPLICATIONS

This application is a continuation of and claims the benefit of priority under 35 U.S.C. §120 to U.S. patent application Ser. No. 12/189,010, filed Aug. 8, 2008, which is a continuation of and claims the benefit of priority under 35 U.S.C. §111(a) of International Application No. PCT/US2007/003645, filed on Feb. 9, 2007, which claims priority to Provisional Application Ser. Nos. 60/771,789, filed Feb. 9, 2006, 60/855,960, filed Nov. 1, 2006 and 60/860,694, filed Nov. 21, 2006, the disclosures of which are incorporated by reference in their entirety.

US GOVERNMENT RIGHTS

This invention was made with United States Government support under Grant No. RO1 GM 067958 awarded by the National Institutes of Health. The United States Government has certain rights in the invention.

BACKGROUND OF THE INVENTION

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator, FTY720 (2-amino-2-[2-(4-octylphenyl)ethyl] propane 1,3-diol), that following phosphorylation, is an agonist at 4 of 5 S1P receptors, revealed that enhancing S1P tone influences lymphocyte trafficking. Further, S1P type 1 receptor ($S1P_1$) antagonists cause leakage of the lung capillary endothelium, which suggests that S1P may be involved in maintaining the integrity of the endothelial barrier in some tissue beds.

Sphingosine 1-phosphate (S1P) is a lysophospholipid mediator that evokes a variety of cellular responses by stimulation of five members of the endothelial cell differentiation gene (EDG) receptor family.

Sphingosine-1-phosphate (S1P) has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing and tumor growth inhibition.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine 1-phosphate phosphohydrolases. Irreversible degradation of S1P is catalyzed by S1P lyase yielding ethanolamine phosphate and hexadecenal.

Currently, there is a need for novel, potent, and selective agents that are agonists of the S1P receptor having enhanced potency, selectivity, and oral bioavailability. In addition, there is a need in the art for identification of, as well as the synthesis and use of such compounds. The present invention satisfies these needs.

SUMMARY

The present invention provides in one aspect compounds that have agonist activity at one or more of the S1P receptors. The compounds are sphingosine analogs that, after phosphorylation, can behave as agonists at S1P receptors. Accordingly, there is provided a compound of formula I:

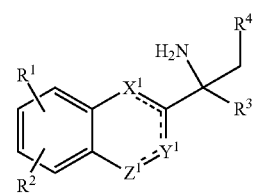

wherein $X^1$, $Y^1$ and $Z^1$ are independently O, $CR^a$, $CR^aR^b$, N, $NR^c$, or S; $R^1$ is hydrogen, halo $(C_1$-$C_{10})$alkyl, or $(C_1$-$C_{10})$alkoxy; $R^2$ is hydrogen, halo, $(C_1$-$C_{20})$alkyl, $(C_1$-$C_{20})$alkoxy; $(C_2$-$C_{26})$alkoxyalkyl; $(C_2$-$C_{20})$alkenyl, $(C_2$-$C_{20})$alkynyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or $R^2$ can be a group having formula II, III, IV, V, or VI:

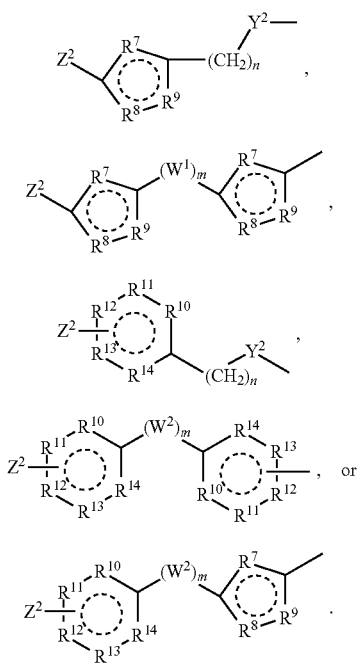

indicates one or more optional double bonds; $Y^2$ is O, C=O, or $CH_2$; $W^1$ is a bond or —$CH_2$—$CH_2$—$CH_2$—; $W^2$ is a bond or —$CH_2$— and m is 1, 2, or 3, or (C=O)$(CH_2)_{1-5}$ and m is 1. Each ≡ represents an optional double bond; n is 0, 1, 2, or 3, and q is 0, 1, 2, or 3.

$R^7$, $R^8$, $R^9$, $R^{10}$, $R^{11}$, $R^{12}$, $R^{13}$, and $R^{14}$ are independently O, S, C, $CR^{15}$, $CR^{16}R^{17}$, C=O, N or $NR^{18}$; $R^{15}$, $R^{16}$ and $R^{17}$ are independently hydrogen, halo, ($C_1$-$C_{10}$)alkyl, ($C_1$-$C_{10}$)alkyl substituted with halo, hydroxy, ($C_1$-$C_{10}$)alkoxy, or cyano; and where $R^{18}$ can be hydrogen or ($C_1$-$C_{10}$)alkyl and at least one of $R^{10}$, $R^{11}$, $R^{12}$, $R^{13}$, or $R^{14}$ is a heteroatom (O, S or N); $Z^2$ is ($C_1$-$C_6$)alkyl, ($C_3$-$C_8$)cycloalkyl, substituted alkyl, ($C_2$-$C_6$) alkenyl, ($C_2$-$C_6$)alkynyl, ($C_6$-$C_{10}$)aryl, alkyl substituted aryl, ($C_7$-$C_{16}$)arylalkyl, or aryl substituted arylalkyl; wherein the alkyl groups of $Z^2$ are optionally substituted with 1, 2, 3, or 4 groups independently are halo, ($C_1$-$C_{10}$)alkoxy or cyano;

$R^3$ is hydrogen, ($C_1$-$C_{10}$)alkyl, or ($C_1$-$C_{10}$)alkoxy; and $R^4$ is hydroxyl (—OH), phosphate (—$OPO_3H_2$), phosphonate (—$CH_2PO_3H_2$), or alpha-substituted phosphonate; $R^c$ is hydrogen, or ($C_1$-$C_{10}$)alkyl. $R^a$, $R^b$, and $R^c$ are independently hydrogen, or ($C_1$-$C_{10}$)alkyl.

The alkyl groups of $R^1$ can be optionally substituted with 1, 2, 3, or 4 substituent groups, where the substituent groups independently are halo, ($C_1$-$C_{10}$)alkoxy or cyano. Any of the alkyl, alkenyl, alkynyl, cycloalkyl, aryl, heterocyclic, or heteroaryl groups of $R^2$ are optionally substituted with 1, 2, 3, or 4 substituent groups, where the substituent groups independently are oxo (=O), imino (=$NR^d$), ($C_1$-$C_{10}$)alkyl, ($C_1$-$C_{10}$)alkoxy, or $C_6$-aryl, or wherein one or more of the carbon atoms in the $R^2$ alkyl groups can be independently replaced with non-peroxide oxygen, sulfur or $NR^c$; the alkyl groups of $R^3$ are optionally substituted with 1, or 2 hydroxy groups; and $R^d$ is hydrogen, or ($C_1$-$C_{10}$)alkyl. The invention includes pharmaceutically acceptable salts or esters of the compounds of formula I.

In another aspect, the invention provides phosphate esters having formula VII.

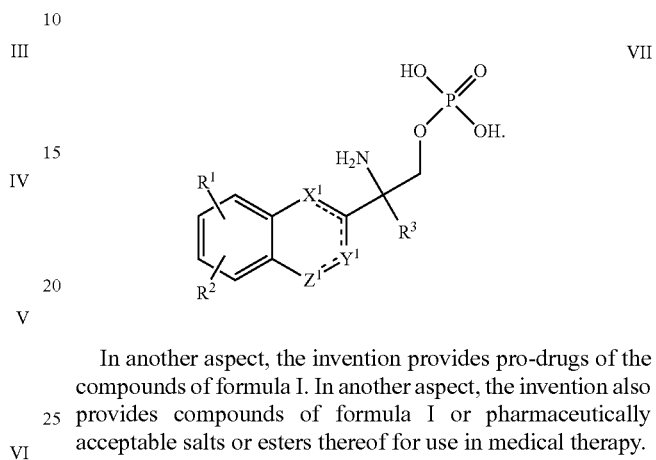

In another aspect, the invention provides pro-drugs of the compounds of formula I. In another aspect, the invention also provides compounds of formula I or pharmaceutically acceptable salts or esters thereof for use in medical therapy.

In another aspect, the present invention provides a method for inhibiting angiogenesis in a tumor, comprising contacting the cancerous cells with an effective amount of a compound of formula I, or a pharmaceutically acceptable salt thereof.

In another aspect, the invention provides a method for modulating the immune system by altering lymphocyte trafficking for treatment of autoimmune diseases or prolongation of allograft transplant survival, said method comprising administering an effective amount of at least one compound of formula I to a subject in need thereof.

In another aspect, the invention provides a method for to preventing, inhibiting or treating neuropathic pain, wherein the method comprises administering an effective amount of at least one compound of formula I or a compound of formula I and a pharmaceutically-acceptable carrier is administered to a subject in need thereof. Pain can be nociceptive or neuropathic in nature. Neuropathic pain is characterized by its chronic nature, an absence of an obvious, direct cause (e.g., tissue damage), hyperalgesia or allodynia. Hyperalgesia is an exaggerated response to a painful stimulus. Allodynia is the perception of normal stimuli as painful (examples include the touch of clothing, warm or cool air, etc.). Neuropathic pain can be a sequel to nerve damage in an extremity such as an arm, or more often a leg. Precipitating events can include trauma, e.g., motor vehicle accidents or amputations (e.g., phantom limb pain). Neuropathic pain can occur due to an adverse effect of drug therapies, e.g., vincristine or paclitaxel (TAXOL™) or can occur as a component of disease pathologies, such as diabetes type 1 or type2, shingles, HIV-1 infections, etc. Typically, neuropathic pain is not responsive to opiates or non-steroidal anti-inflammatory drugs such as aspirin.

In another aspect, the invention provides a method for repairing vascular injury following catheterization, comprising contacting the lumen of the affected vessel with an effective amount of the compound of formula I. In another aspect, the invention includes coating indwelling stents with a compound of formula I.

In another aspect, the present invention provides compositions and methods for the use of S1P analogs to prevent and inhibit vascular restenosis following vascular injury. For example, the injury can be due to balloon angioplasty. In another aspect, the present invention includes a method for treating subjects to prevent vascular restenosis.

In another aspect, the present invention provides compositions and methods for the use of sphingosine analogs (including S1P pro-drugs) to prevent asthma attacks. In one aspect, the asthma could be due to over production of cysteinyl leukotrienes. In another aspect, the present invention includes a method for treating subjects to treat asthma.

In another aspect, the present invention provides compositions and methods for the use of sphingosine analogs of formula I (including S1P pro-drugs) to treat obesity.

In another aspect, the present invention provides compositions and methods for the use of sphingosine analogs (including S1P pro-drugs) to normalize blood lipid composition. In one aspect, blood low density lipoprotein (LDL or 'bad cholesterol') levels could be lowered. In another aspect, blood triglyceride levels could be lowered.

In another aspect, the present invention provides compositions and methods for the use of S1P analogs and S1P pro-drugs for the prevention and treatment of arteriosclerosis.

In another aspect, the present invention provides compositions and methods for the use of S1P analogs and S1P pro-drugs for the treatment of neoplastic disease. In one aspect, this treatment is effected by application of SIT receptor antagonists that are efficacious by virtue of their anti-angiogenic properties. In another aspect, the treatment is effected by administration of sphingosine analogs of formula I that inhibit the multiple substrate lipid kinase.

In another aspect, the present invention provides compositions and methods for the use of S1P analogs and S1P pro-drugs for the treatment of neurodegenerative diseases. In one aspect, the treatment is for senile dementia of the Alzheimers type.

In another aspect, the invention provides a compound of formula I, or a pharmaceutically acceptable salt thereof for use in medical treatment (for example, treatment of neoplastic disease, treatment of neuropathic pain, treatment of autoimmune disease, prolongation of allograft survival).

In another aspect, the invention provides a method for the use of a compound of formula I or a pharmaceutically acceptable salt thereof to prepare a medicament for inhibiting tumor growth, metastasis or tumor angiogenesis in a mammalian species (for example, a human).

In another aspect, the invention provides for the use of a compound of formula I or a pharmaceutically acceptable salt thereof to prepare a medicament for treating an autoimmune disease or prolonging allograft survival in a mammalian species (for example, a human).

In another aspect, the invention provides for the use of a compound of formula I or a pharmaceutically acceptable salt thereof to prepare a medicament for treating neuropathic pain in a mammalian species (for example, a human).

In another aspect, the invention provides a method for assessing a compound of formula I (e.g., S1P receptor pro-drugs) as a substrate for sphingosine kinase types 1 or 2, in vitro and in vivo. In another aspect, the invention includes a method of assessing a compound of formula I for binding to designated receptor sites comprising in vivo or in vitro, with an amount of a compound of formula I effective to bind said receptors. Tissue comprising ligand bound designated S1P receptor sites can be used to measure the selectivity of test compounds for specific receptor subtypes, or can be used as a tool to identify potential therapeutic agents for the treatment of diseases, by contacting said agents with said ligand-receptor complexes, and measuring the extent of displacement of the ligand or binding of the agent.

In another aspect, the invention provides novel intermediates and processes disclosed herein that are useful for preparing compounds of formula I, including the generic and specific intermediates as well as the synthetic processes described herein.

In another aspect, the present invention provides synthetic schemes and methods of use of compounds having formula I and analogs or derivatives thereof. In another aspect, the invention provides synthetic and modification schemes for preparing analogs and derivatives of the compounds of formula I, as well as compositions and methods for the use of such analogs and derivatives.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying description below. Other features, objects, and advantages of the invention will be apparent from the description and drawings, and from the claims.

DETAILED DESCRIPTION

Figure 1:
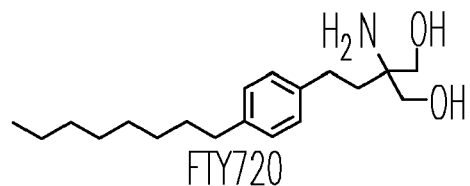
FIG. 1 is an illustration of three S1P agonists FTY720, AA151 compound XXIX and additional compounds of formula I.
Figure 1:
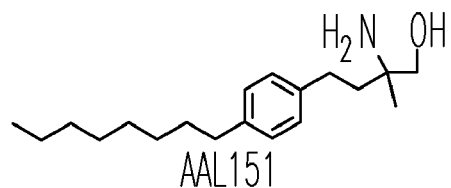
Figure 1:
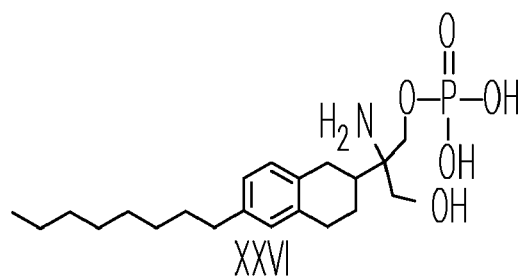
Figure 1:
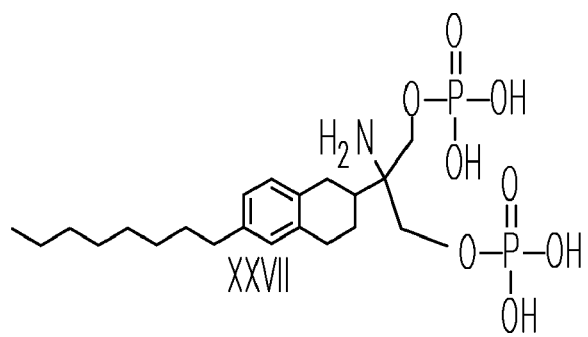
Figure 1:
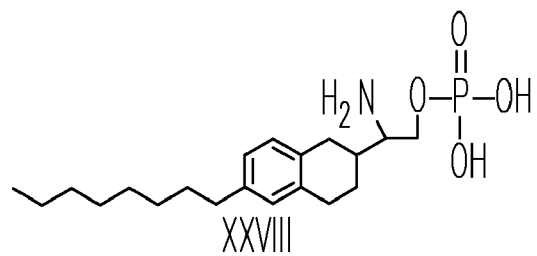
Figure 1:
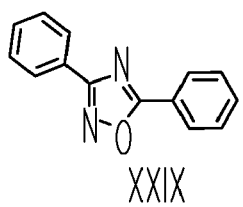

The following abbreviations are used herein: S1P, sphingosine-1-phosphate; $S1P_{1-5}$ S1P receptor types; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transcriptase polymerase chain reaction.

In describing and claiming the invention, unless otherwise defined, all technical and scientific terms used herein have the same meaning as commonly understood by one of ordinary skill in the art to which this invention belongs. Although any materials and methods similar or equivalent to those described herein can be used in the practice or testing of the present invention, the preferred materials and methods are described herein. Each of the following terms has meaning associated with it in this section. Specific and preferred values listed below for radicals, substituents, and ranges are for illustrations only; they do not exclude other defined values or other values within defined ranges for the radicals and substituents.

The terms "a," "an," "the," "at least one," and "one or more" are used interchangeably. Thus, for example, a composition that comprises "an" element means one element or more than one element.

The term "receptor agonists" are compounds that mimic the action of S1P at one or more of its receptors but may have differing potency or efficacy.

The term "receptor antagonists" are compounds that 1) lack intrinsic agonist activity and 2) block agonist (e.g., S1P) activation of the S1P receptor(s), often in a manner that is both fully surmountable and reversible ('competitive antagonist').

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" means an amount sufficient to produce a selected effect. For example, an effective amount of an S1P receptor antagonist is an amount that decreases the cell signaling activity of the S1P receptor.

A "functional" molecule is a molecule in a form in which it exhibits a property by which it is characterized. By way of example, a functional enzyme is one which exhibits the characteristic catalytic activity by which the enzyme is characterized.

The term "inhibit" refers to the ability of a disclosed compound to reduce or impede a described function. Preferably, inhibition is by at least 10%, more preferably by at least 25%, even more preferably by at least 50%, and most preferably, the function is inhibited by at least 75%.

"Instructional material" includes a publication, a recording, a diagram, or any other medium of expression which can be used to communicate the usefulness of the disclosed compounds in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains a disclosed compound or be shipped together with a container which contains the identified compound. Alternatively, the instructional material may be shipped separately from the container with the intention that the instructional material and the compound be used cooperatively by the recipient.

The term "parenteral" means not through the alimentary canal but by some other route such as subcutaneous, intramuscular, intraspinal, or intravenous.

The term "pharmaceutically acceptable carrier" includes any of the standard pharmaceutical carriers, such as a phosphate buffered saline solution, water and emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

The term "purified" and similar terms relate to the isolation of a molecule or compound in a form that is substantially free (at least 75% free, preferably 90% free, and most preferably at least 95% free) from other components normally associated with the molecule or compound in a native environment. The term "purified" does not necessarily indicate that complete purity of the particular molecules achieved during the process. A "very pure" compound refers to a compound that is greater than 90% pure. A "highly purified" compound refers to a compound that is greater than 95% pure.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition or preventing or eliminating said symptoms.

The disclosed compounds are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours, "rt" for room temperature, and "rac" for racemic mixture).

The values listed below for radicals, substituents, and ranges, are for illustration only; they do not exclude other defined values or other values within defined ranges for the radicals and substituents. The disclosed compounds include compounds of formula I having any combination of the values, specific values, more specific values, and preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl or trifluoromethyl and the like. The term "$C_1$-$C_{20}$ alkyl" refers to a branched or linear alkyl group having from one to nine carbons. Non-limiting examples include, but are not limited to, methyl, ethyl, n-propyl, iso-propyl, butyl, iso-butyl, sec-butyl, tert-butyl, pentyl, hexyl, heptyl, octyl and the like. The term "$C_2$-$C_{20}$ alkenyl", refers to an olefinically unsaturated branched or linear group having from two to nine carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, octenyl and the like. The term ($C_2$-$C_{20}$) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like. The term "($C_1$-$C_{10}$)alkoxy or alkoxyl" refers to an alkyl group attached through an oxygen atom. Examples of ($C_1$-$C_{10}$)alkoxy can be methoxy, ethoxy, propoxy, isopropoxy, butoxy, iso-butoxy, sec-butoxy, pentoxy, 3-pentoxy, or hexyloxy and the like. The term "$C_3$-$C_{12}$ cycloalkyl", can be cyclopropyl, cyclobutyl, cyclopentyl, cyclohexyl, cycloheptyl, cyclooctyl and the like.

The term "optionally substituted" refers to zero, one, two, three or four substituents, wherein the substituents are each independently selected. Each of the independently selected substituents may be the same or different than other substituents.

The term "($C_6$-$C_{10}$)aryl" refers to a mono or bicyclic carbocyclic ring system having one or two aromatic rings including, but not limited to, phenyl, benzyl, naphthyl, tetrahydronaphthyl, indanyl, indenyl, and the like.

The term "aryl($C_1$-$C_{20}$)alkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, and the like.

The term "optionally substituted aryl" includes aryl compounds having zero, one, two, three or four substituents, and a substituted aryl includes aryl compounds having one, two, three or four substituents, wherein the substituents include groups such as, for example, alkyl, halo, or amino substituents.

The "($C_2$-$C_{10}$)heterocyclic group" refers to an optionally substituted mono- or bicyclic carbocyclic ring system containing one, two, or three heteroatoms (optionally in each ring) wherein the heteroatoms are oxygen, sulfur, and nitrogen.

The term "($C_4$-$C_{10}$)heteroaryl" refers to an optionally substituted mono- or bicyclic carbocyclic ring system containing one, two, or three heteroatoms (optionally in each ring) wherein the heteroatoms are oxygen, sulfur, and nitrogen. Non-limiting examples of heteroaryl groups include furyl, thienyl, pyridyl, and the like.

The term "bicyclic" represents either an unsaturated or saturated stable bridged or fused bicyclic carbon ring. The bicyclic ring may be attached at any carbon atom which affords a stable structure. Typically a bicyclic ring system can have from about 7- to about 12 atoms in the ring system. The term includes, but is not limited to, naphthyl, dicyclohexyl, dicyclohexenyl, and the like.

The term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, K, and the like if such counterions are present.

A "derivative" of a compound refers to a chemical compound that may be produced from another compound of similar structure in one or more steps, such as replacement of hydrogen by an alkyl, acyl, or amino group.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

The term "pharmaceutically-acceptable salt" refers to salts which retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto.

An "effective amount" means an amount sufficient to produce a selected effect. For example, an effective amount of an S1P receptor agonist is an amount that decreases the cell signaling activity of the S1P receptor.

The disclosed compounds can contain one or more asymmetric centers in the molecule. In accordance with the present disclosure any structure that does not designate the stereochemistry is to be understood as embracing all the various optical isomers, as well as racemic mixtures thereof.

The disclosed compounds may exist in tautomeric forms and the invention includes both mixtures and separate individual tautomers. For example, the following structure:

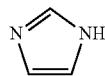

is understood to represent a mixture of the structures:

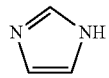

as well as

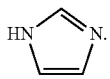

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

An "S1P modulating agent" refers a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," refers to all of the S1P receptor subtypes (for example, the S1P receptors $S1P_1$, $S1P_2$, $S1P_3$, $S1P_4$, and $S1P_5$), unless the specific subtype is indicated.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof, of the compound, which possess the useful properties described herein, such as the S,R; S,S; R,R; or R,S diastereomers. It is well known in the art how to prepare such optically active forms (for example, by resolution of the racemic form by recrystallization techniques, by synthesis from optically-active starting materials, by chiral synthesis, or by chromatographic separation using a chiral stationary phase) and how to determine S1P agonist activity using the standard tests described herein, or using other similar tests which are well known in the art. In addition, some compounds may exhibit polymorphism.

Potential uses of an S1P receptor agonist pro-drugs ($S1P_1$ receptor type selective agonists preferred) include, but are not limited to, altering lymphocyte trafficking as a method of treatment for autoimmune pathologies such as uveitis, type I diabetes, rheumatoid arthritis, inflammatory bowel diseases, and, most particularly, multiple sclerosis. "Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

In addition, the disclosed compounds can be used for altering lymphocyte trafficking as a method for prolonging allograft survival, for example solid organ transplants, treatment of graft vs. host disease, bone marrow transplantation, and the like.

In addition, the disclosed compounds can be used to inhibit autotaxin. Autotaxin, a plasma phosphodiesterase, has been demonstrated to undergo end product inhibition. Autotaxin hydrolyzes several substrates to yield lysophosphatidic acid and sphingosine 1-phosphate, and has been implicated in cancer progression and angiogenesis. Therefore, S1P receptor agonist pro-drugs of the disclosed compounds can be used to inhibit autotaxin. This activity may be combined with agonism at S1P receptors or may be independent of such activity.

In addition, disclosed compounds can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, the disclosed compounds can be used to inhibit S1P lyase. This inhibition could be in concert with S1P receptor activity, or be independent of activity at any S1P receptor.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

"Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

The present invention is also includes pharmaceutical compositions comprising the compounds of formula I. More particularly, such compounds can be formulated as pharmaceutical compositions using standard pharmaceutically acceptable carriers, fillers, solubilizing agents and stabilizers known to those skilled in the art. For example, a pharmaceutical composition comprising a compound of formula I, or analog, derivative, or modification thereof, as described herein, is used to administer the appropriate compound to a subject.

The compounds of formula I are useful for treating a disease or disorder including administering to a subject in need thereof of a therapeutically acceptable amount of a compound of formula I, or a pharmaceutical composition comprising a therapeutically effective amount of a compound of formula I, and a pharmaceutically-acceptable carrier.

The disclosed compounds and method are directed to sphingosine 1-phosphate (S1P) analogs that have activity as receptor agonists or antagonists at one or more S1P receptors, specifically the $S1P_1$, S1P and $S1P_5$ receptor types. The disclosed compounds and method include both compounds that have a phosphate moiety as well as compounds with hydrolysis-resistant phosphate surrogates such as phosphonates, alpha-substituted phosphonates particularly where the alpha substitution is a halogen and phosphothionates.

The values listed below for radicals, substituents, and ranges, are for illustration only; they do not exclude other defined values or other values within defined ranges for the radicals and substituents.

$X^1$, $Y^1$ and $Z^1$ are independently O, CH, $CH_2$, $CHCF_3$, N, NH, or S.

Another value for $X^1$, $Y^1$ and $Z^1$ is $CH_2$.

$R^1$ can be hydrogen, fluorine, chlorine, bromine, trifluoromethyl, methoxy, $(C_1-C_6)$alkyl, $(C_1-C_6)$haloalkyl, or $(C_1-C_6)$alkyl substituted with, alkoxy or cyano.

Additional values for $R^1$ are hydrogen, trifluoromethyl, or —$CH_2CF_3$.

More additional values for $R^1$ are alkyl-substituted aryl, aryl-substituted alkyl, or aryl-substituted arylalkyl.

More additional values for $R^1$ are benzyl, phenylethyl, or methyl benzyl.

Compounds having formula I can have an $R^2$ group that includes a chain having the structure —$CH_2$—$CH_2$—O—$CH_2$—$CH_2$—O—.

Values for $R^2$ include

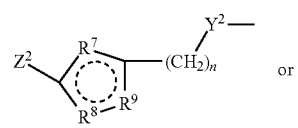

II or

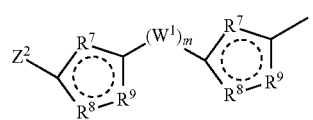

III

Additional values for $R^2$ having formula II are

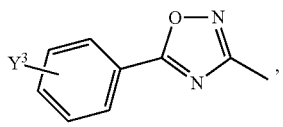

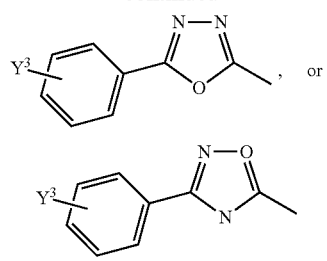

, or where $Y^3$ is $(CH_3)_3C$—, $CH_3CH_2(CH_3)_2C$—, $CH_3CH_2CH_2$—, $CH_3(CH_2)_2CH_2$—, $CH_3(CH_2)_4CH_2$—, $(CH_3)_2CHCH_2$—, $(CH_3)_3CCH_2$—, $CH_3CH_2O$—, $(CH_3)_2CHO$—, or $CF_3CH_2CH_2$— or a group having the formula:

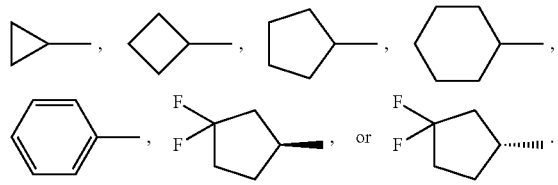

An additional value for $R^2$ having formula II (para substituted 3,5-diphenyl-(1,2,4)-oxadiazole) is;

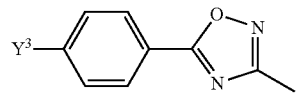

Another value for $R^2$ having formula II is;

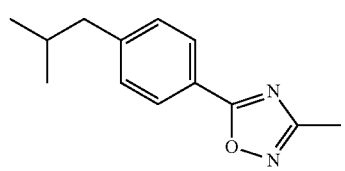

Another value for $R^2$ having formula II is;

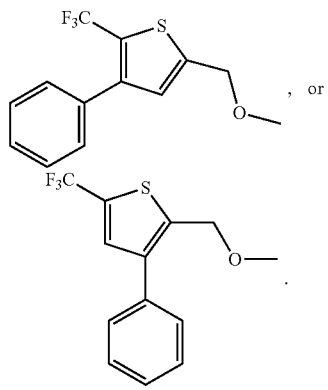

Additional values for R² having formla III are;

[Structure: 4-phenyl-5-trifluoromethyl-thiophene connected to 3-methyl-1,2,4-oxadiazole]

[Structure: 4-phenyl-5-trifluoromethyl-thiophene connected to 5-methyl-1,3,4-oxadiazole], or

[Structure: 4-phenyl-5-trifluoromethyl-thiophene connected to 3-methyl-1,2,4-oxadiazole isomer].

Another value for R² having formula III is;

[Structure: 4-phenyl-5-trifluoromethyl-thiophene-2-ylmethoxy]

Additional values for R² include (C₁-C₂₀)alkyl, (C₁-C₂₀)alkoxy, or (C₂-C₂₆)alkoxyalkyl.

More additional values for R² include (C₁-C₁₀)alkyl, (C₂-C₁₀)alkenyl and (C₂-C₁₄)alkynyl or (C₁-C₁₀)alkoxy optionally substituted with carbonyl (C=O) or oxime (C=NR^d) groups.

Additional values for R² include methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.

Another value for R³ is methyl, hydroxymethyl, ethyl, hydroxyethyl, propyl, hydroxypropyl, or isopropyl.

Another value for R³ is methyl, hydroxymethyl, ethyl, or hydroxyethyl.

A value for R⁴ is hydroxy, or phosphate (—OPO₃H₂).

A specific compound has the formula

[Structure: naphthalene with R¹, R², and substituent with H₂N, R³, R⁴].

Additional compounds have formulas

VIII

[Structure VIII: octyl-tetrahydronaphthalene with H₂N, HO, OH substituents]

IX

[Structure IX: heptyloxy-tetrahydronaphthalene with H₂N, HO, OH substituents]

X

[Structure X: octyl-tetrahydronaphthalene with NH₂, methyl, OH substituents]

XI

[Structure XI: butoxyethoxy-tetrahydronaphthalene with H₂N, HO, OH substituents]

XII

[Structure XII: methoxypentoxy-tetrahydronaphthalene with H₂N, HO, OH substituents]

XIII

[Structure XIII: heptyloxy-dihydronaphthalene with H₂N, HO, OH substituents]

XIV

[Structure XIV: heptyloxy-dihydronaphthalene isomer with H₂N, HO, OH substituents]

-continued
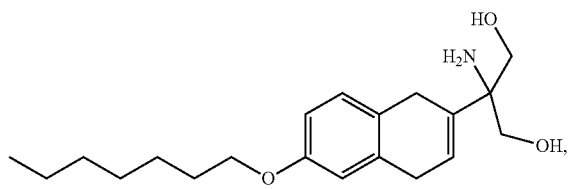
XV
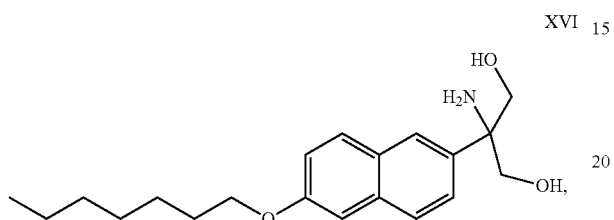
XVI
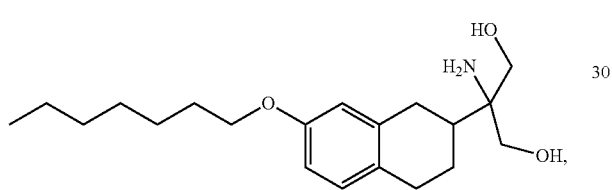
XVII
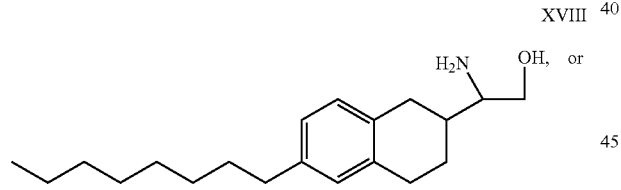
XVIII or
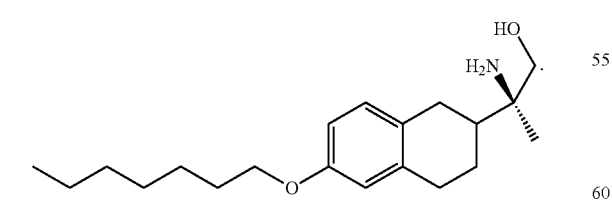
XIX
Additional compounds having formula I include compounds above or in FIG. 1 where one of more of the hydrogen atoms from a hydroxy group is replaced with a phosphate group —OP(=O)(OH)$_2$.
Additional compounds of formula I are illustrated in table 1, below.
TABLE 1
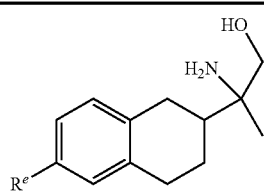
or
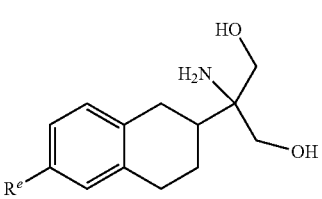
| Compound | $R^e$ |
|---|---|
| XX | 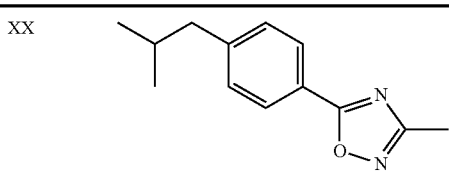 |
| XXI | 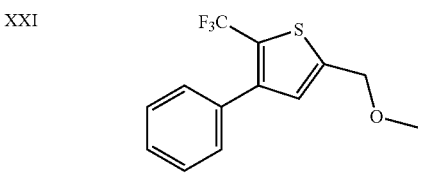 |
| XXII | 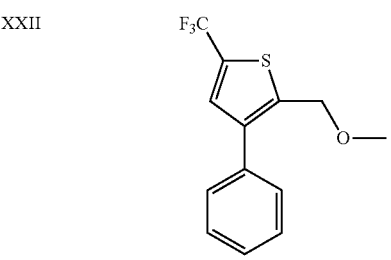 |
| XXIII | 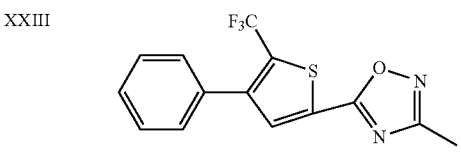 |
| XXIV | 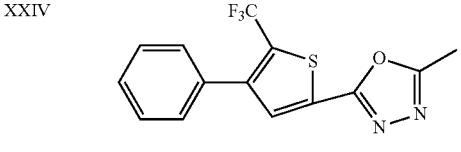 |
| XXV | 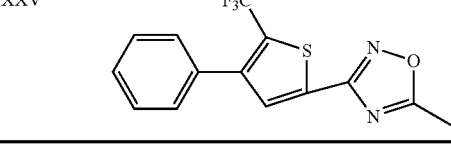 |

In another aspect, the invention provides S1P receptor prodrug compounds having the general structure of formula I, is provided by a compound with a mono-substituted tetralin ring system that has the formula VIII. In some embodiments of formula I, the structure (e.g., IX and X) has only a single chiral center and that the amino carbon is pro-chiral, e.g., will become chiral following enzyme-catalyzed phosphorylation.

Without wishing to be bound by any particular theory, it is expected that the compounds described herein are pro-drugs, e.g., are activated by phosphorylation of the primary alcohol to form the mono-phosphorylated analog. Additionally, the active drugs are expected to be agonists at the S1P type 1 receptor.

In cases where compounds of formula I are sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Mon-limiting examples of amines include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

The compounds of formula I can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and mixtures thereof.

The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1 to about 25 weight percent, preferably from about 0.5-10 weight percent. The concentration in a semi-solid or solid composition such as a gel or a powder will be about 0.1-5 wt-%, preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a dose will be in the range of from about 0.1 to about 10 mg/kg of body weight per day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method includes a kit comprising an inhibitor compound of formula I and instructional material which describes administering the inhibitor compound or a composition comprising the inhibitor compound to a cell or a subject. This should be construed to include other embodiments of kits that are known to those skilled in the art, such as a kit comprising a (preferably sterile) solvent for dissolving or suspending the inhibitor compound or composition prior to administering the compound or composition to a cell or a subject. Preferably, the subject is a human.

In accordance with the disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the disclosed compounds.

Processes for preparing compounds of formula I or for preparing intermediates useful for preparing compounds of formula I are provided as further embodiments. Intermediates useful for preparing compounds of formula I are also provided as further embodiments. The processes are provided as further embodiments and are illustrated in the schemes herein wherein the meanings of the generic radicals are as given above unless otherwise qualified.

Figure 2:
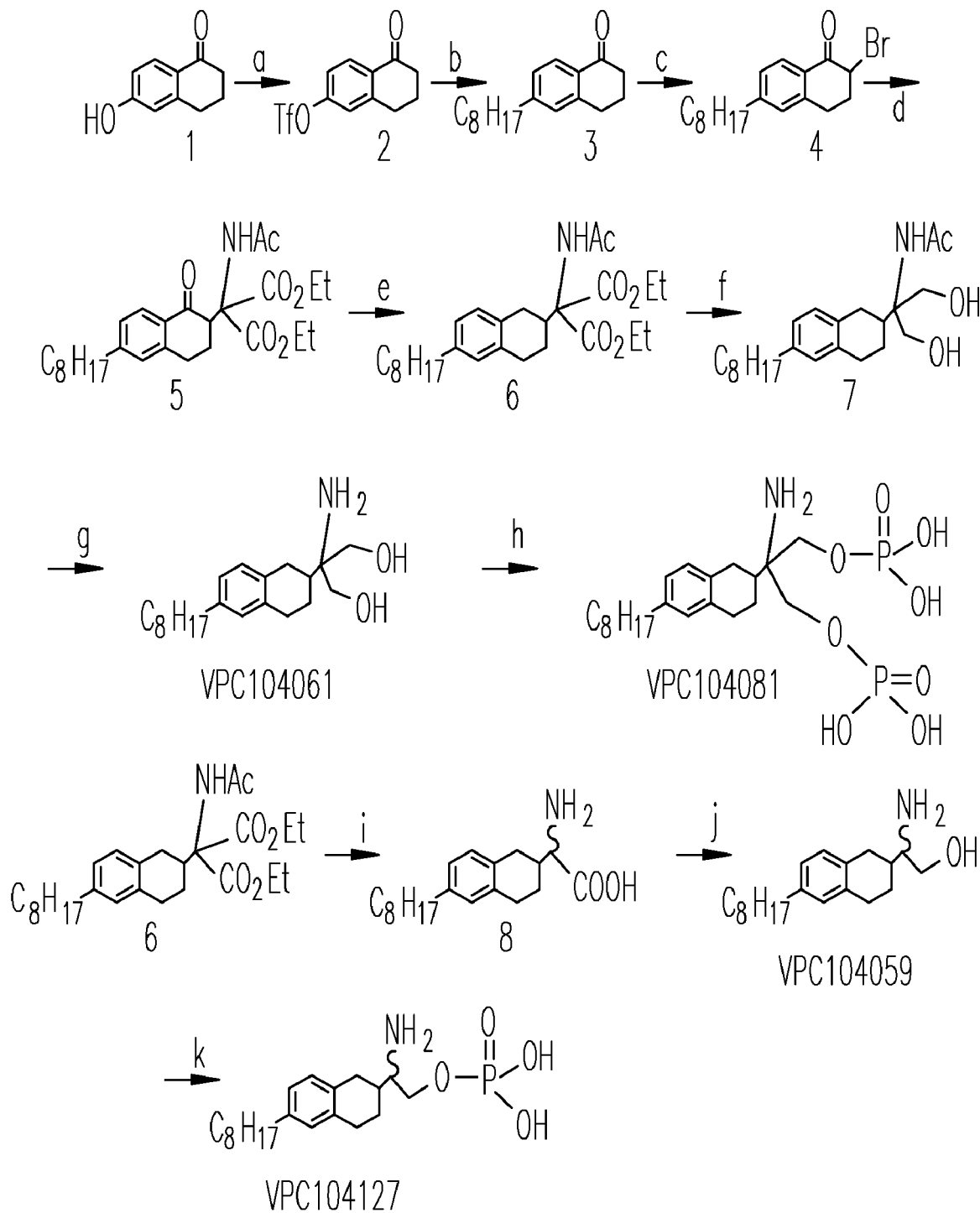
FIGS. 2, 3 and 4 are schemes illustrating syntheses of compounds of formula I.

An example of the synthesis of several disclosed compounds is illustrated in Scheme 1 (FIG. 2). The reagents and conditions are as follows: a) $Tf_2O$, 2,6-lutidine, $CH_2Cl_2$, 0° C., 2 h, 93%; b) 1-octene, 9-BBN, $K_3PO_4$, KBr, $H_2O$, $Pd(PPh_3)_4$, 65° C., 2 h, 82%; c) $CuBr_2$, EtOAc, $CHCl_3$, reflux 6 h, 80%; d) NaH, N-acetamido-diethylmalonate, DMF, 0° C.-rt, overnight, 75%; e) $Et_3SH$, $TiCl_4$, $CH_2Cl_2$, rt, 12 h, 65%; f) $LiBH_4$, rt, THF, 48 h, 33%; g) LiOH, $H_2O$, MeOH, THF, 50° C., 5 h, 75%; h) $P_2O_5$, $H_3PO_4$, 100° C., 2 h, 37%; i) 12M HCL, MeOH, reflux, 2 h; j) $LiAlH_4$, THF, reflux, 12 h, 21%, two steps; k) $P_2O_5$, $H_3PO_4$, 100° C., 2 h, 50%.

The invention is now described with reference to the following Examples and Embodiments. Without further description, it is believed that one of ordinary skill in the art can, using the preceding description and the following illustrative examples, make and utilize the disclosed compounds. The following working examples therefore, are provided for the purpose of illustration only and specifically point out the preferred embodiments, and are not to be construed as limiting in any way the remainder of the disclosure. Therefore, the examples should be construed to encompass any and all variations which become evident as a result of the teaching provided herein.

EXAMPLES

Example 1

Trifluoromethanesulfonic acid 5-oxo-5,6,7,8-tetrahydro-naphthalen-2-yl ester (2)

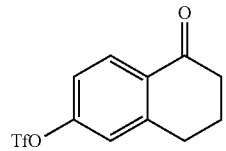

Trifluoromethanesulfonic anhydride (1.7 mL, 10 mmol) was added slowly over 1 hour to a solution of 6-hydroxy-1-tetralone (1.62 g, 10 mmol) and 2,6-lutidine (1.28 mL, 10 mmol) in dry dichloromethane (10 mL) cooled to 0° C. After 1 hour the solution was diluted with dichloromethane (10 mL) and washed with 1 M hydrochloric acid (20 mL). The organic layer was re-extracted with dichloromethane (50 mL) and the combined organics washed with 1 M hydrochloric acid (10 mL). The organics were dried over magnesium sulfate and concentrated under vacuum. The residue was purified by column chromatography (Silica gel, $CH_2Cl_2$) to provide 2.7 g of compound 2 (93%).

$^1$H NMR (300 MHz, $CDCl_3$) δ 2.13 (p, 2H, J. 6.22 Hz), 2.63 (t, 2H, J=6.95 Hz), 2.98 (t, 2H, J=6.22 Hz), 7.15 (m, 2H), 8.07 (m, 1H); $^{13}$C NMR δ 23.08, 29.88, 38.92, 116.74, 119.81, 121.56, 130.14, 132.58, 147.38, 152.52, 196.53.

Example 2

6—Octyl-3,4-dihydro-2H-naphthalen-1-one (3)

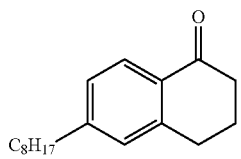

9-BBN (0.5 M solution in THF, 20.2 mL, 10.1 mmol) was added to 1-octene (1.6 mL, 10.1 mmol) at room temperature. The solution was stirred, at room temperature, overnight. After this time, $K_3PO_4$ (2.93 g, 13.8 mmol), $Pd(Ph_3P)_4$ (191 mg, 0.17 mmol, 1.8 mol %), KBr (1.2 g, 10.1 mmol) and degassed $H_2O$ (0.18 mL, 10 mmol) were added. This was followed by a solution of compound 2 (2.7 g, 9.2 mmol) in dry degassed THF (10 mL). The reaction mixture was heated at 65° C. under argon for 2 hours. After cooling, the solution was acidified to pH 1 and extracted into EtOAc (100 mL). The aqueous layer was re-extracted with EtOAc (50 mL) and the combined organics washed with $H_2O$ (20 mL) and brine (40 mL). The organic layer was dried over magnesium sulfate and concentrated under vacuum. The residue was purified by column chromatography (Silica gel, 5% EtOAc in hexanes) to provide 1.93 g of compound 3 (82%).

$^1$H NMR (300 MHz, $CDCl_3$) δ 0.85 (t, 3H, J=6.95 Hz), 1.24 (bs, 10H), 1.58 (p, 2H, J=6.95 Hz), 2.06 (p, 2H, J=5.85 Hz), 2.57 (t, 4H, J=6.95 Hz), 2.87 (t, 2H, J=6.22 Hz), 7.01 (s, 1H), 7.06 (d, 1H, J=8.05 Hz), 7.91 (d, 1H, J=8.06 Hz); $^{13}$C NMR δ 14.32, 22.88, 23.61, 29.44, 29.55, 29.66, 29.96, 31.32, 32.08, 36.31, 39.33, 127.12, 127.45, 128.73, 130.75, 144.70, 149.28, 198.09.

Example 3

2-Bromo-6-octyl-3,4-dihydro-2H-naphthalen-1-one (4)

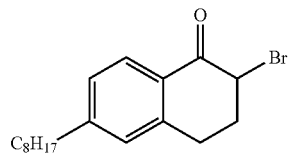

Cupric bromide (3.34 g, 15.0 mmol) was heated at reflux in ethyl acetate (10 mL) with stirring. To this was added compound 3 (1.93 g, 7.5 mmol) in chloroform (10 mL). The reaction was heated at reflux for a further 6 hours and cooled. Copper bromide and cupric bromide residues were filtered off and the filtrate was decolorized with activated charcoal and filtered through a bed of Celite and washed with ethyl acetate (4×50 mL). The solvent was removed under reduced pressure and the residue was purified by column chromatography (Silica gel, 2% EtOAc in hexanes) to provide 2.02 g of compound 4 (80%).

$^1$H NMR (300 MHz, $CDCl_3$) δ 0.87 (t, 3H, J=6.95 Hz), 1.26 (bs, 10H), 1.61 (p, 2H, J=6.96 Hz), 2.46 (m, 2H), 2.62 (t, 2H, J=7.69 Hz), 2.86 (dt, 1H, J=16.34 Hz, 4.39 Hz), 3.27 (dt, 1H, J=16.83 Hz, 4.39 Hz), 4.69 (t, 1H, J=4.02 Hz), 7.07 (s, 1H), 7.14 (d, 1H, J=8.05 Hz), 7.99 (d, 1H, J=8.05 Hz); $^{13}$C NMR δ 14.34, 22.88, 26.42, 29.44, 29.57, 29.64, 31.25, 32.08, 32.32, 36.39, 127.75, 128.00, 128.73, 129.00, 144.30, 150.39, 190.54.

Example 4

2-Acetylamino-2-(6-octyl-1-oxo-1,2,3,4-tetrahydro-naphthalen-2-yl)-malonic acid diethyl ester (5)

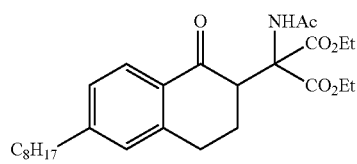

Sodium hydride (720 mg, 18.0 mmol) 60% in mineral oil was suspended in dry DMF (10 mL) and a solution of diethyl acetamidomalonate (3.26 g, 15 mmol) in dry DMF (10 mL) was added. The solution was stirred at 0° C. for 3 hours until the anion had formed. A solution of 4 (2.02 g, 6.0 mmol) in dry DMF (10 mL) was added and the solution warmed to room temperature and stirred overnight. The mixture was poured into distilled water (50 mL), in an ice-bath, acidified to pH 3 with 1M hydrochloric acid and extracted with ethyl acetate (3×50 mL). The organic phases were washed with brine (2×30 mL) and dried over magnesium sulfate and concentrated under vacuum. The residue was purified by column chromatography (Silica gel, 40% EtOAc in hexanes) to provide 2.12 g of compound 5 (75%).

$^1$H NMR (300 MHz, CDCl$_3$) δ 0.85 (t, 3H, J=6.22 Hz), 1.24 (m, 16H), 1.58 (p, 2H, J=6.95 Hz), 1.97 (s, 3H), 2.59 (t, 2H, J=7.32 Hz), 2.83-3.21 (m, 4H), 3.88 (dd, 1H, J=14.00 Hz, 3.68 Hz), 4.14-4.32 (m, 4H), 6.86 (s, 1H), 7.03 (s, 1H), 7.07 (d, 1H, J=8.69 Hz), 7.84 (d, 1H, J=8.36 Hz); $^{13}$C NMR δ 14.05, 14.16, 14.30, 22.85, 23.31, 26.98, 29.40, 29.49, 29.61, 29.98, 31.28, 32.05, 36.32, 56.16, 62.40, 63.13, 66.33, 127.16, 127.63, 128.78, 144.84, 150.07, 166.38, 168.70, 169.83, 197.63.

Example 5

2-Acetylamino-2-(6-octyl-1,2,3,4-tetrahydro-naphthalen-2-yl)-malonic acid diethyl ester (6)

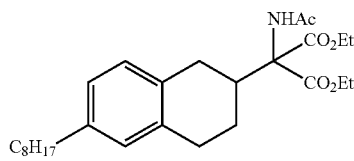

To a solution of triethylsilane (1.3 ml, 8.2 mmol) in 5 ml of CH$_2$Cl$_2$ was added compound 5 (1 g, 2.1 mmol) in 5 ml of CH$_2$Cl$_2$. The reaction mixture was stirred at room temperature under Ar and TiCl$_4$ (0.09 ml, 8.2 mmol) was added dropwise. The resulting solution was stirred for 12 hours, cooled to 0° C. and quenched by slow addition of 10 ml of saturated NaHCO$_3$. The aqueous layer was extracted with CH$_2$Cl$_2$ (3×30 mL). The combined organic layers were washed with brine (2×30 mL) and dried over magnesium sulfate and concentrated under vacuum. The residue was purified by column chromatography (Silica gel, 20% EtOAc in hexanes) to provide 630 mg of compound 6 (65%).

$^1$H NMR (300 MHz, CDCl$_3$) δ 0.87 (t, 3H, J=6.46 Hz), 1.26 (m, 16H), 1.58 (p, 2H, J=6.79 Hz), 2.03 (s, 3H), 2.28 (b, 1H), 2.49-2.68 (m, 4H), 2.82-2.92 (m, 2H), 4.20-4.34 (m, 4H), 6.69 (s, 1H), 6.89-7.05 (m, 3H); $^{13}$C NMR δ 14.21, 14.25, 14.37, 22.92, 23.37, 25.48, 29.50, 29.63, 29.72, 29.76, 30.39, 31.93, 32.13, 35.78, 40.33, 62.46, 62.79, 68.80, 126.04, 128.81, 129.30, 132.85, 136.28, 140.66, 150.07, 167.63, 168.32, 169.42.

Example 6

N-[2-Hydroxy-1-hydroxymethyl-1-(6-octyl-1,2,3,4-tetrahydro-naphthalen-2-yl)-ethyl]-acetamide (7)

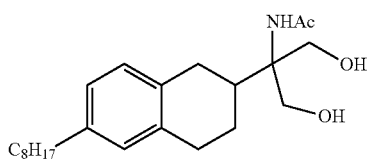

Lithium borohydride (2M solution in THF, 0.88 ml, 1.76 mmol) was added to compound 6 (200 mg, 0.44 mmol) in 5 ml THF at 0° C. The reaction mixture was stirred at room temperature for 48 hours and diluted with 40 ml ethyl acetate. The solution was washed with brine (2×20 mL) and dried over magnesium sulfate and concentrated under vacuum. The residue was purified by column chromatography (Silica gel, 4% MeOH in CH$_2$Cl$_2$) to provide 55 of mg compound 7 (33%).

$^1$H NMR (300 MHz, CDCl$_3$) δ 0.88 (t, 3H, J=6.56 Hz), 1.29 (m, 10H), 1.57 (p, 2H, J=6.25 Hz), 1.94-1.98 (m, 2H), 2.05 (s, 3H), 2.33 (m, 1H), 2.51 (t, 2H, J=7.32), 2.60-2.85 (m, 4H), 3.69 (d, 2H, J=11.61), 3.89 (dd, 2H, J=11.61 Hz, 7.25 Hz), 6.22 (s, 1H), 6.88-6.99 (m, 3H); $^{13}$C NMR δ 14.38, 22.92, 24.20, 24.35, 29.52, 29.66, 29.73, 29.95, 30.32, 31.94, 32.14, 35.78, 38.26, 63.55, 64.34, 64.46, 126.18, 128.85, 129.30, 133.06, 136.22, 140.75, 172.40.

Example 7

2-Amino-2-(6-octyl-1,2,3,4-tetrahydro-naphthalen-2-yl)-propane-1,3-diol (VPC104061)

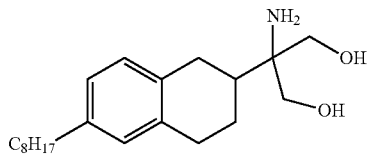

A solution of compound 7 (53 mg, 0.14 mmol) and LiOH.H$_2$O (45 mg, 1.1 mmol) in MeOH (3 ml), THF (1.5 ml) and water (3 ml) was stirred at 50° C. for 5 hours and diluted with ethyl acetate (20 ml). The solution was washed with brine (2×10 mL) and dried over magnesium sulfate and concentrated under vacuum. The residue was purified by column chromatography (Silica gel, 50% MeOH in CH$_2$Cl$_2$) to provide 35 mg of compound VPC104061(75%).

$^1$H NMR (300 MHz, CDCl$_3$) δ 0.88 (t, 3H, J=6.17 Hz), 1.29 (m, 10H), 1.56 (p, 2H, J=6.17 Hz), 1.82-1.98 (m, 2H), 2.51 (t, 2H, J=6.95), 2.58-2.88 (m, 5H), 3.19 (b, 4H), 3.61 (d, 2H, J=10.98), 3.73 (d, 2H, J=10.61 Hz), 6.87-6.98 (m, 3H); $^{13}$C NMR δ 14.37, 22.93, 24.02, 29.32, 29.53, 29.70, 29.75, 29.85, 30.26, 31.94, 32.14, 35.08, 39.58, 57.74, 66.13, 66.19, 126.09, 128.81, 129.39, 133.28, 136.26, 140.64. MS (ESI) m/z 334.1 [M+H]$^+$.

Example 8

Phosphoric acid mono-[2-amino-2-(6-octyl-1,2,3,4-tetrahydro-naphthalen-2-yl)-3-phosphonooxypropyl] ester (VPC104081)

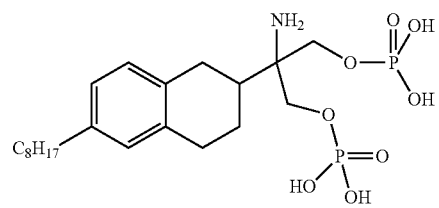

Phosphorus pentoxide (2.0 g, 14 mmol) in phosphoric acid (85% in water, 2 ml, 29 mmol) was added to VPC104061 (25 mg, 0.07 mmol). The mixture was stirred at 100° C. for 2 hours and cooled to 0° C. The product was precipitated by adding water (14 mg, 37%). MS (ESI) m/z 494.4 [M+H]$^+$.

Example 9

Amino-(6-octyl-1,2,3,4-tetrahydro-naphthalen-2-yl)-acetic acid (8)

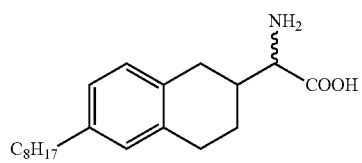

Compound 6 (300 mg, 0.65 mmol) was added to 12 M HCl (10 ml). The mixture was heated to reflux and MeOH (5 ml) was added until the mixture became homogenous. Reflux was continued for 2 hours until the starting material was consumed as determined by thin layer chromatography (TLC). The reaction mixture was concentrated under reduced pressure and co-evaporated with MeOH and diethyl ether multiple times. The desired compound 8 was recrystallized from diethyl ether and hexanes to provide a light brown solid and used directly for the next reaction.

Example 10

2-Amino-2-(6-octyl-1,2,3,4-tetrahydro-naphthalen-2-yl)-ethanol (VPC 104059)

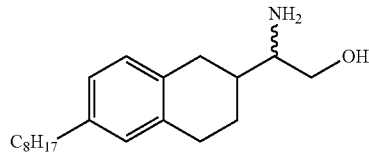

The amino acid 8 prepared in Example 9 was added to a refluxing solution of lithium aluminum hydride (62 mg, 1.63 mmol) in TI-IF (10 ml). The reaction mixture was heated at reflux for 12 hours, subsequently cooled to 0° C. and 10 M NaOH was added and stirred for 20 minutes. Ethyl acetate (20 ml) was added and the mixture was filtered through Celite and magnesium sulfate. The filtrate was concentrated under vacuum and purified by column chromatography (Silica gel, 50% MeOH in CH$_2$Cl$_2$) to provide 41 mg of the product, VPC104059 (21%, two steps).

$^1$H NMR (300 MHz, CDCl$_3$) δ 0.88 (t, 3H, J=6.39 Hz), 1.28 (m, 10H), 1.55 (p, 2H, J=7.16 Hz), 1.67-2.11 (m, 3H), 2.48 (t, 2H, J=7.69), 2.56-2.83 (m, 5H), 3.19 (b, 4H), 3.47-3.75 (m, 2H), 6.82-6.96 (m, 3H); $^{13}$C NMR δ 13.34, 22.58, 26.45, 29.14, 29.21, 29.29, 29.47, 31.70, 31.90, 32.26, 35.40, 47.56, 125.64, 128.36, 128.86, 128.93, 133.19, 139.93, MS (ESI) m/z 303.9 [M+H]$^+$.

Example 11

Phosphoric acid mono-[2-amino-2-(6-octyl-1,2,3,4-tetrahydro-naphthalen-2-yl)-ethyl] ester (VPC104127)

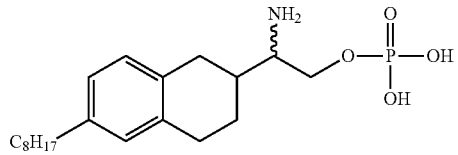

Phosphorus pentoxide (1.5 g, 10.5 mmol) in phosphoric acid (85% in water, 1.5 ml, 22 mmol) was added to VPC104059 (25 mg, 0.08 mmol). The mixture was stirred at 100° C. for 2 h and cooled to 0° C. The product was precipitated by adding water (10 mg, 50%). MS (ESI) m/z 384.2 [M+H]$^+$.

Example 12

Synthesis of structure (X)

Figure 3:
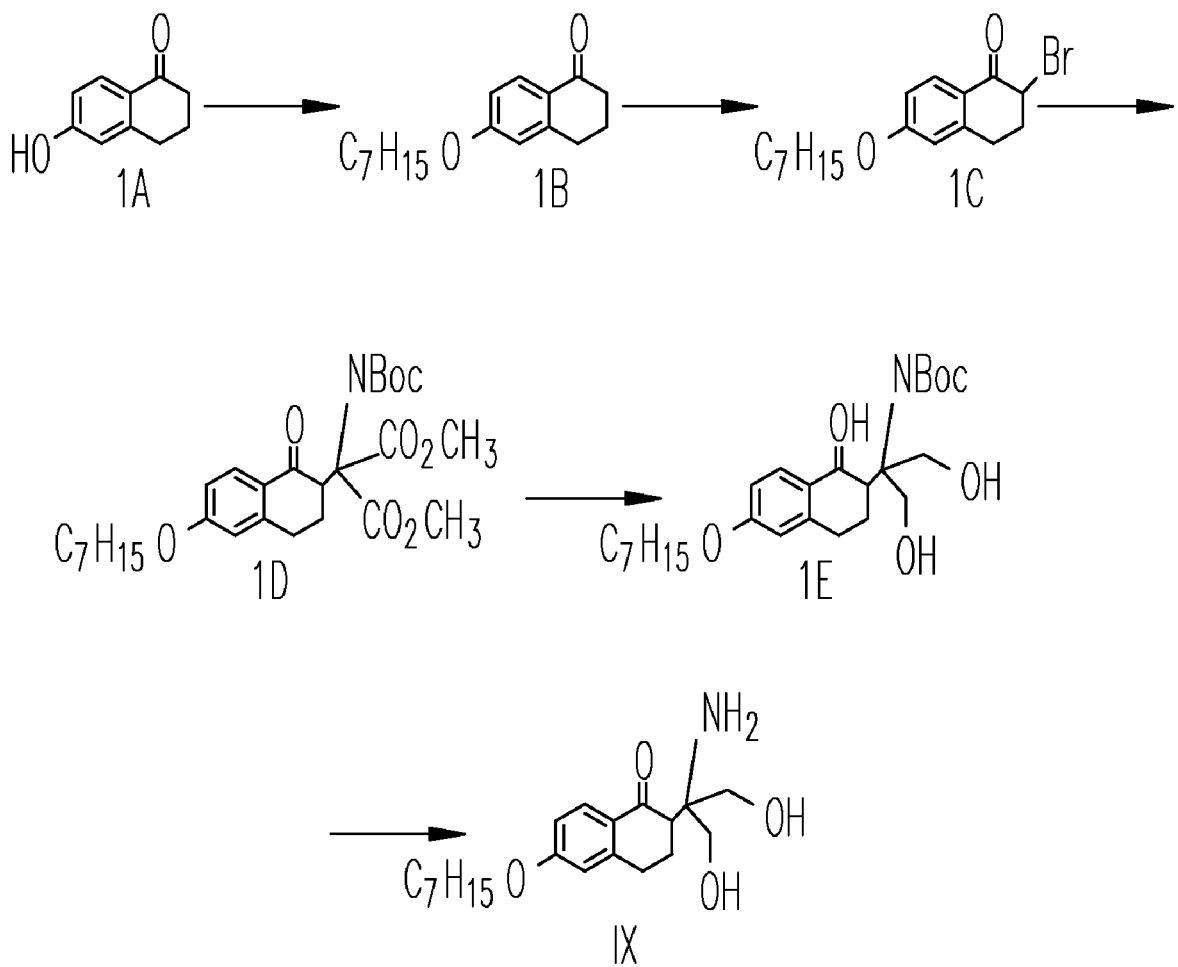

The synthesis of an ether containing compound having formula IX is illustrated in Scheme 2 (FIG. 3). Keto-alcohol 1A, is converted to the keto-ether 1B, using standard reagents and techniques. The keto-ether is halogenated to provide halo-ether 1C in a manner similar to Example 3. The halo-ether is alkylated to provide diester-ether 1D, in a manner similar to the procedure described in Example 4. The diester is converted to ether-triol 1E, using standard reducing agents known in the art. The triol is converted to a diol and deprotected using standard methods known in the art, to provide compound IX.

Example 13

2-Acetylamino-2-(6-octyl-1-hydroxy-1,2,3,4-tetrahydro-naphthalen-2-yl)-malonic acid diethyl ester (A)

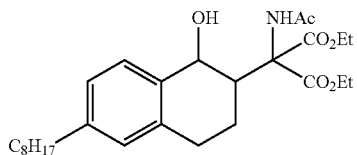

To a solution of sodium borohydride (75 mg, 2.00 mmol) in 5 ml of ethanol at room temperature is added 2-acetylamino-2-(6-octyl-1-oxo-1,2,3,4-tetrahydro-naphthalen-2-yl)-malonic acid diethyl ester (compound 5) (1.00 g, 2.1 mmol) in 5 ml of ethanol. The reaction mixture is stirred at room temperature under argon for an additional hour, quenched by the addition of water (20 mL) and methylene chloride (20 mL). The organic layer is removed and the aqueous layer is extracted with methylene chloride (2×20 mL). The combined organic layers were washed with brine (2×20 mL) and dried over magnesium sulfate and concentrated under vacuum. The residue is purified by column chromatography (silica gel, 20% ethyl acetate in hexanes) to provide 755 mg of compound A (75%).

Example 14

2-Acetylamino-2-(6-octyl-3,4-dihydro-naphthalen-2-yl)-malonic acid diethyl ester (B)

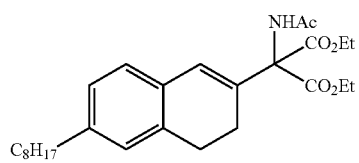

Figure 4:
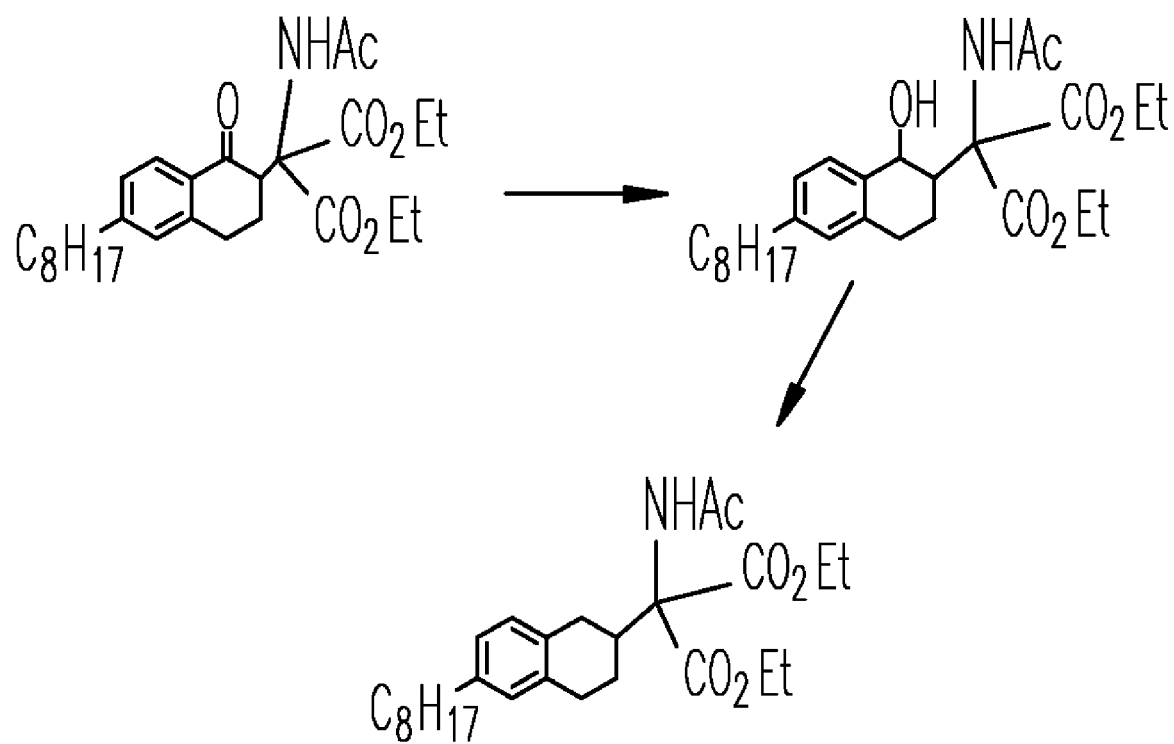

2-Acetylamino-2-(6-octyl-1-hydroxy-1,2,3,4-tetrahydro-naphthalen-2-yl)-malonic acid diethyl ester (compound A, 755 mg, 1.58 mmol)) is dissolved in acetic anhydride (5 mL) followed at 0° C. by a catalytic amount of ferric chloride (66 mg, 0.4 mmol). The reaction is stirred at 0° C. for an additional 2 hours, and 20 mL of diethyl ether is added. The reaction is carefully poured into 50 mL of ice cold water and the organic layer quickly separated. The organic layer is re-extracted with methylene chloride (2×20 mL) and the combined organic layers were washed once with brine (20 mL) and dried over magnesium sulfate. The organic layer is concentrated under vacuum and the residue is purified by column chromatography (silica gel, 10% ethyl acetate in hexanes) to provide 458 mg of compound B (60%). The complete synthesis is illustrated in FIG. 4.

Example 14

Sphingosine Kinase Assay

Figure 5B:
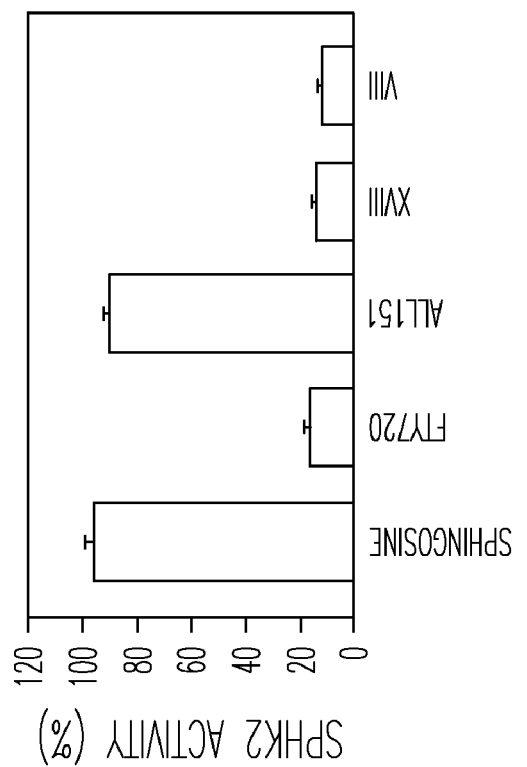
FIGS. 5A, 5B and 6 illustrate the results of sphingosine kinase type 2 (SPHK2) activity for S1P agonist compounds FTY720, AA151, VIII and XVIII.
Figure 5A:
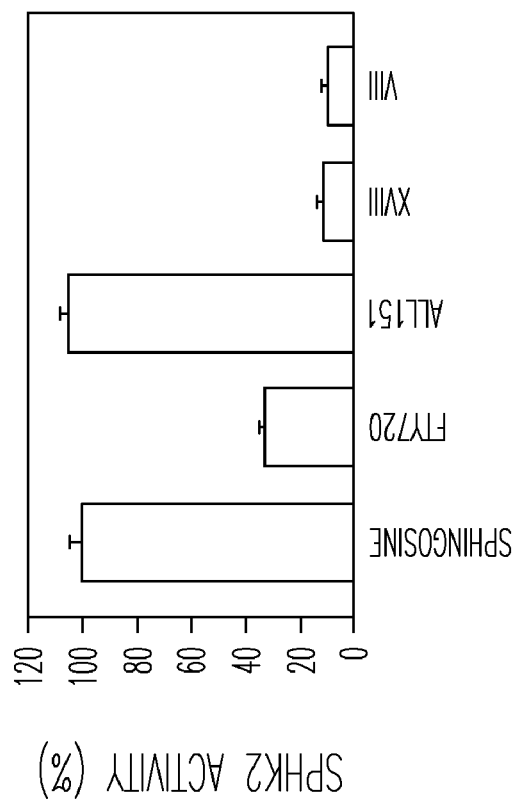
Figure 6:
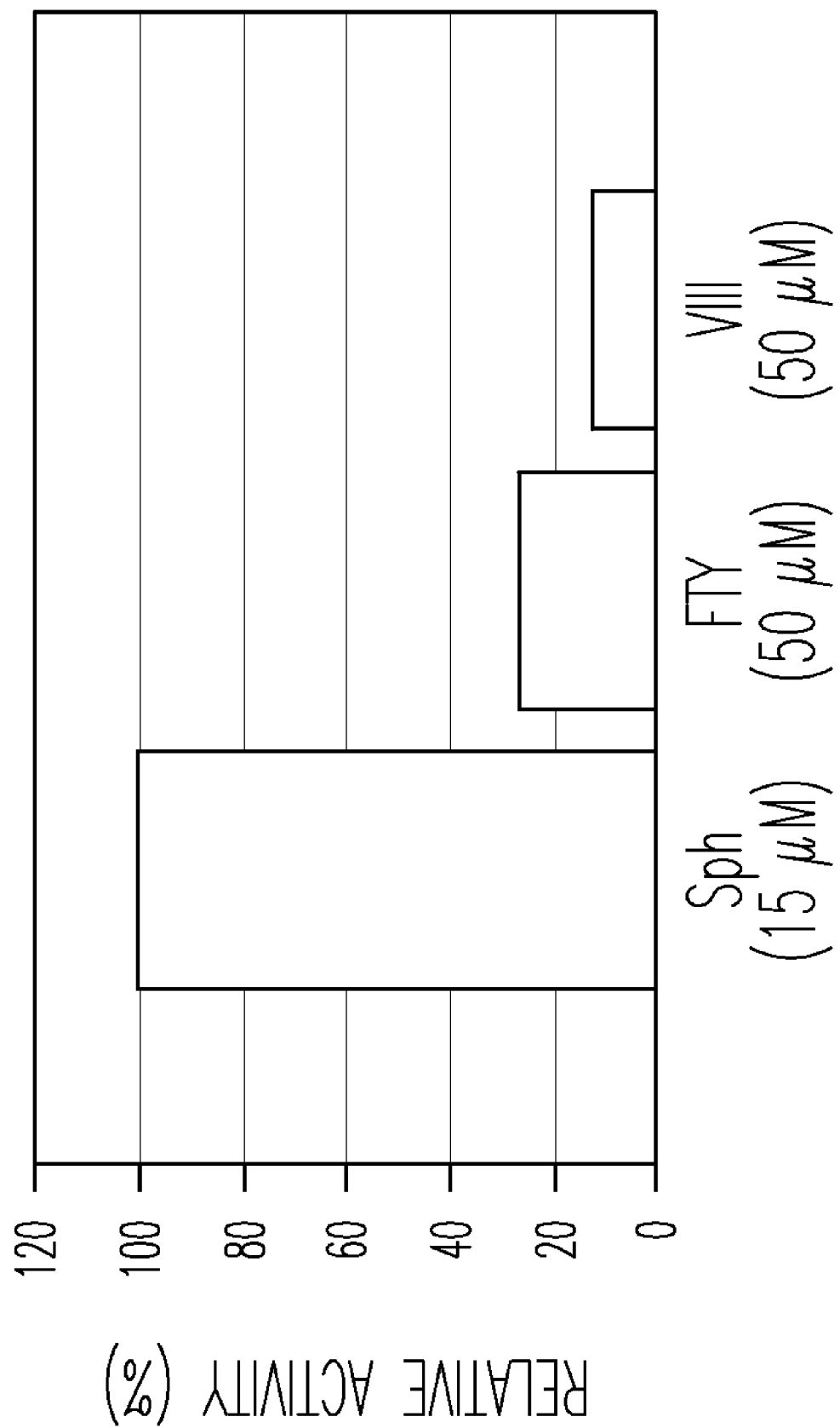

Recombinant sphingosine kinase type 2 (SPHK2) is prepared by forcing the expression of the mouse or human recombinant enzyme by transfecting the relevant plasmid DNA into HEK293T cells. After about 60 hours, cells are harvested, broken and the non-microsomal (e.g., soluble) fraction is retained. The broken cell supernatant fluid containing the recombinant enzyme is mixed with test compounds (FTY720, AA151, VIII and XVIII) (5-50 micromolar) and γ-32P-ATP and incubated for 0.5-2.0 hours at 37° C. The lipids in the reaction mixture are extracted into an organic solvent and displayed by normal phase thin layer chromatography. The radio-labeled bands are detected by autoradiography, scraped from the plate and quantified by scintillation counting. In the histogram shown, (FIGS. 5A, 5B and 6) sphingosine was present at 15 μM, and the test compounds were at a concentration of 50 μM, incubation time was 20 minutes.

Example 15

GTPγS-35 binding Assay

This assay illustrates agonist activation of G protein coupled receptors (GPCRs) in isolation. The assay forces expression concomitantly of a recombinant GPCR (e.g., the S1P1-5 receptor) and each of the three subunits (typically, α-2, β-1, or γ-2) of a heterotrimeric G protein in a HEK293T cell by transfecting the cell with four plasmid DNAs encoding the respective proteins. About 60 hours after transfection the cells are harvested, opened, and the nucleus discarded. The crude microsome is prepared from the remainder. Agonist (e.g., S1P) stimulation of the receptor-G protein complex on the microsomes results in the exchange of GTP for GDP on the α-subunit in a dose-dependent manner. The GTP-bound a-subunit is detected using a GTP analog (GTPγS-35), which is a radionuclide (sulfur-35) labeled phosphothioate that is not hydrolyzed to GDP. The microsomes with the adherent G proteins are collected by filtration and the bound GTPγS-35 quantified in a liquid scintillation counter. The assay yields relative potency ($EC_{50}$ values) and maximum effect (efficacy, $E_{max}$a Antagonist activity is detected as rightward shifts in the agonist dose-response curve in the presence of a fixed amount of antagonist. If the antagonist behaves competitively, the affinity of the receptor/antagonist pair ($K_1$) can be determined.

Figure 7:
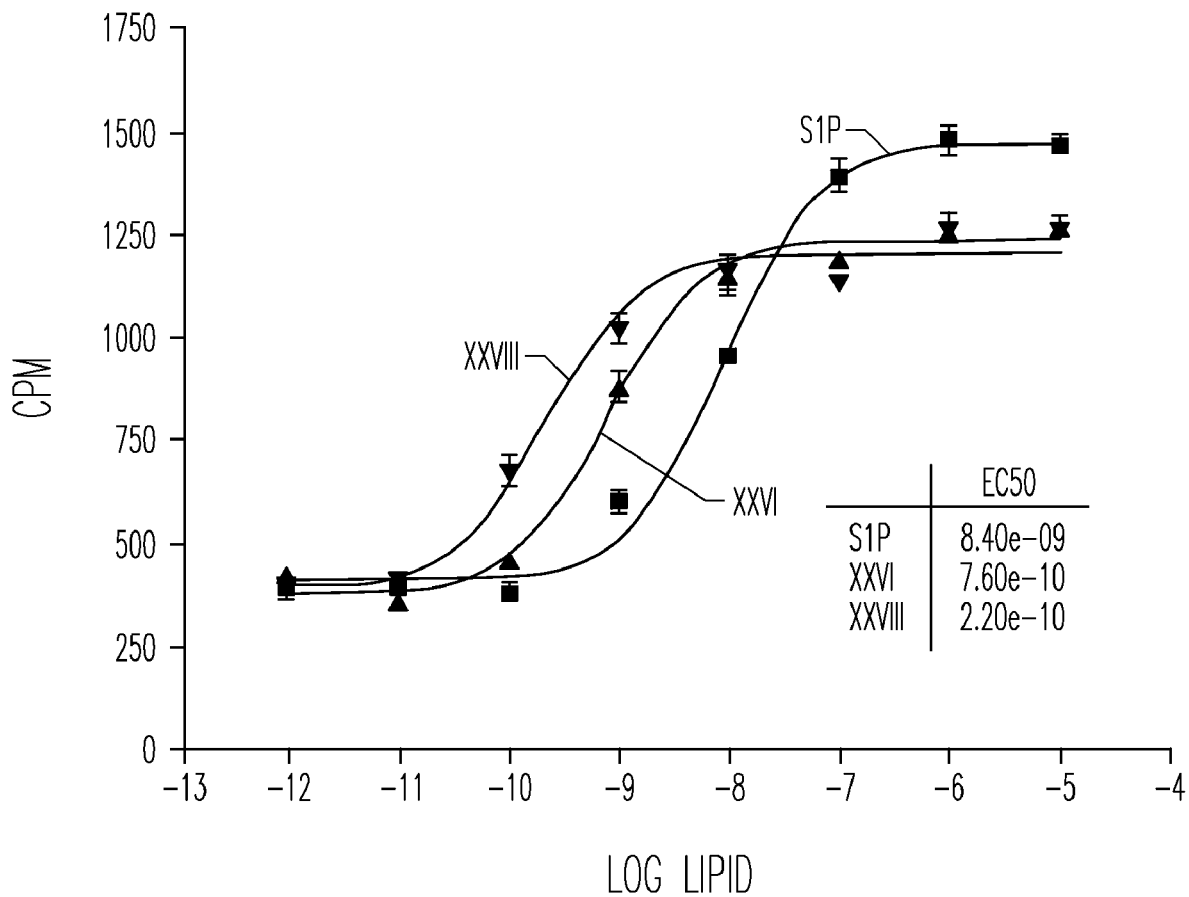
FIGS. 7 and 8 graphically illustrate the results of a broken cell $GTP\gamma^{35}S$ binding assay for the human $S1P_1$ receptor, testing S1P and compounds XXVI, XXVII and XXVIII.
Figure 8:
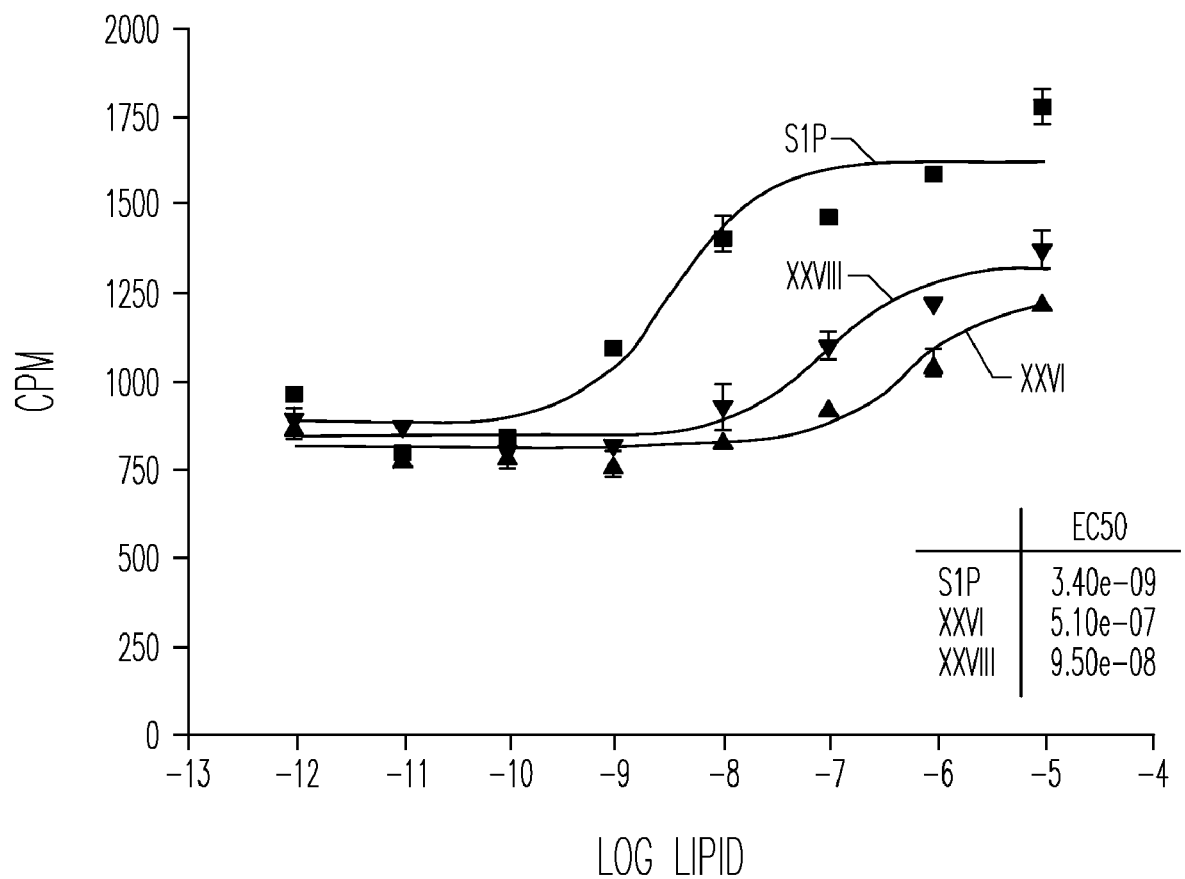

The phosphorylated forms of compound VIII (a mixture of mono, XXVI, and dephosphorylated, XXVII, isomers) and compound XXVIII are low potency, partial agonists at the $S1P_3$ receptor (See FIG. 8.). Compounds XXVI, XXVII and XXVIII are more potent at $S1P_1$ and less potent at $S1P_3$, relative to S1P. (See FIG. 7.) The assay was performed as described in Davis, M. D., J. J. Clemens, T. L. Macdonald and K. R. Lynch (2005) "S1P Analogs as Receptor Antagonists" Journal of Biological Chemistry, vol. 280, pp. 9833-9841.

Example 16

Lymphopenia Assay

Compounds (e.g., primary alcohols such as compound VIII) are dissolved in 2% hydroxypropyl beta-cyclodextrin and introduced into groups of mice by oral gavage at doses from 0.01, 1.0 and 10 mg/kg body weight. After 24 hours and 48 hours, the mice are lightly anesthetized and ca. 0.1 ml of blood is drawn from the orbital sinus. The number of lymphocytes (in thousands per microliter of blood; normal is 4-11) is determined using a Hemavet blood analyzer. In the histogram showing compound VIII, the 100% value for the vehicle treated mouse was 7.5 at 24 hours; at 96 hours it was 5. There were three mice/group, the strain was mixed sv129× C57BL/6. Active compounds (e.g., compound VIII and compound XXVIII) are dissolved in acidified DMSO at 20 mM, and diluted 1:20 into 2% hydroxypropyl beta-cyclodextrin in water with mixing. This solution is introduced into mice by intraperitoneal (i.p.) injection at doses of 0.01, 1.0 and 10 mg/kg body weight.

Figure 9:
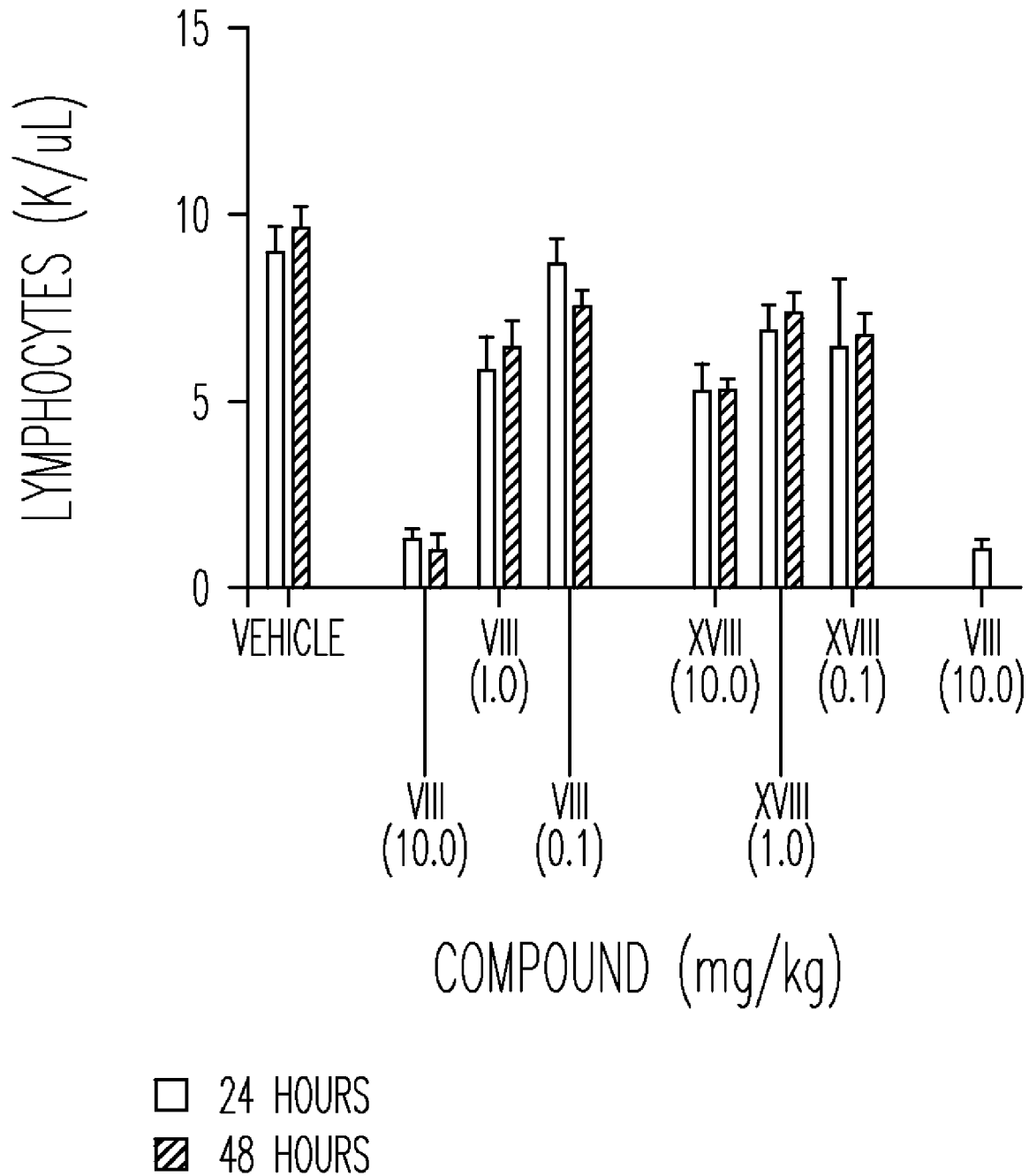
FIG. 9 is graphically illustrates total lymphocyte counts (K/μl) 24 hours (left bar of each group) and 48 hours (right bar of each group) after an oral dose of the test compounds are administered to mice.

In FIG. 9 the results of an assay using compound VIII and compound XXVIII administered via oral gavage are graphically illustrated. The total lymphocyte counts (k/μl) 24 hours after an IV dose of compound VIII is reported.

Figure 10:
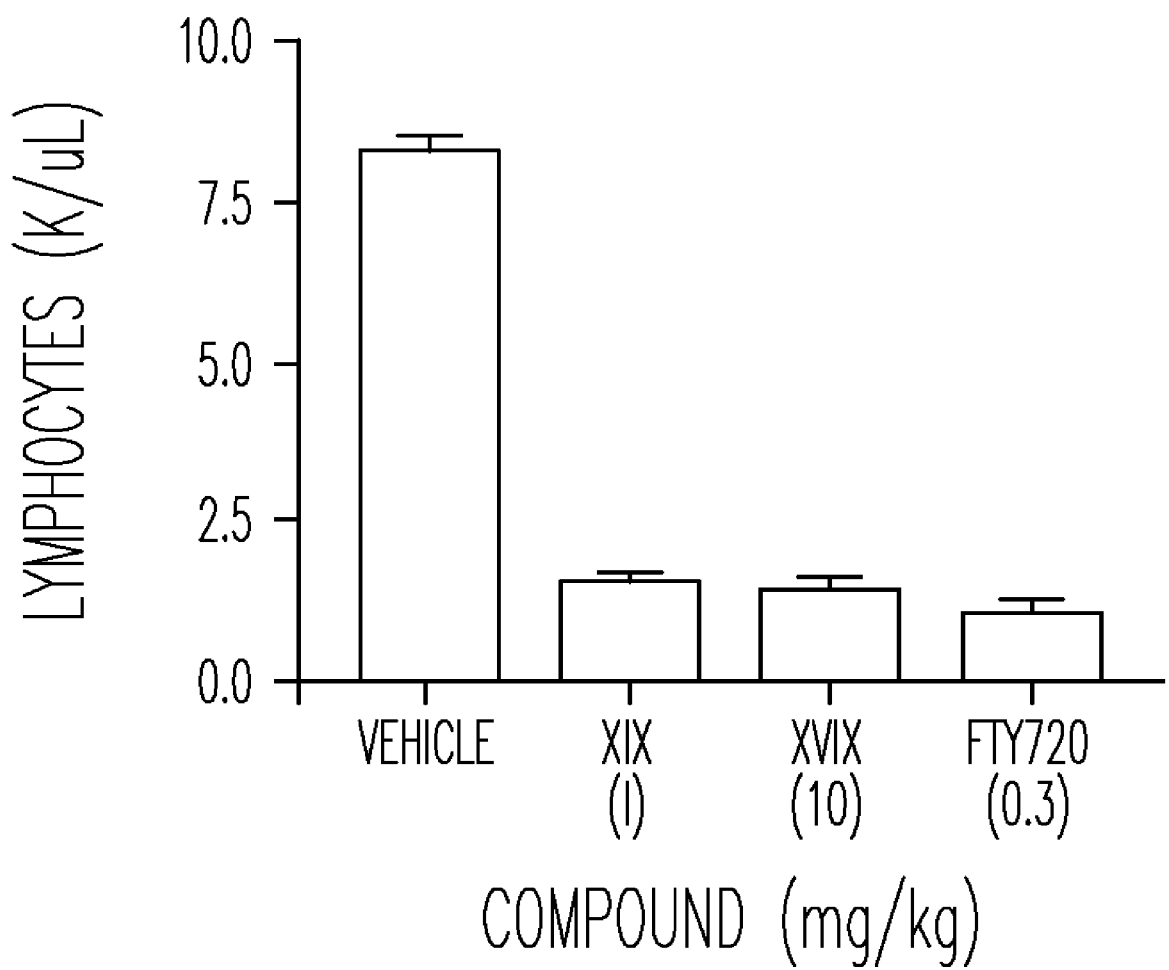
FIG. 10 is graphically illustrates total lymphocyte counts (k/μl) 18 hours after an oral dose of the test compounds are administered to mice.

Compounds were dissolved in 2% hydroxypropyl β-cyclodextrin and administered to sets of three, 12 week old C57Bl/6 female mice by oral gavage (PO). At 18 hours post dosing, blood was drawn from the orbital sinus and lymphocyte numbers were determined with a Hemavet blood analyzer. Doses were: compound XXIX (1 mg/kg), compound VIII (10 mg/kg), and FTY720 (0.3 mg/kg). Compound XXIX, 3,5-diphenyl-1,2,4-oxadiazole, is a S1P1 receptor agonist described by Li et al. (Journal Medicinal Chemistry, vol. 48, p. 6169 (2005)) was used as a comparison. The results are illustrated in FIG. 10.

Example 17

Heart Rate Assay

Figure 11:
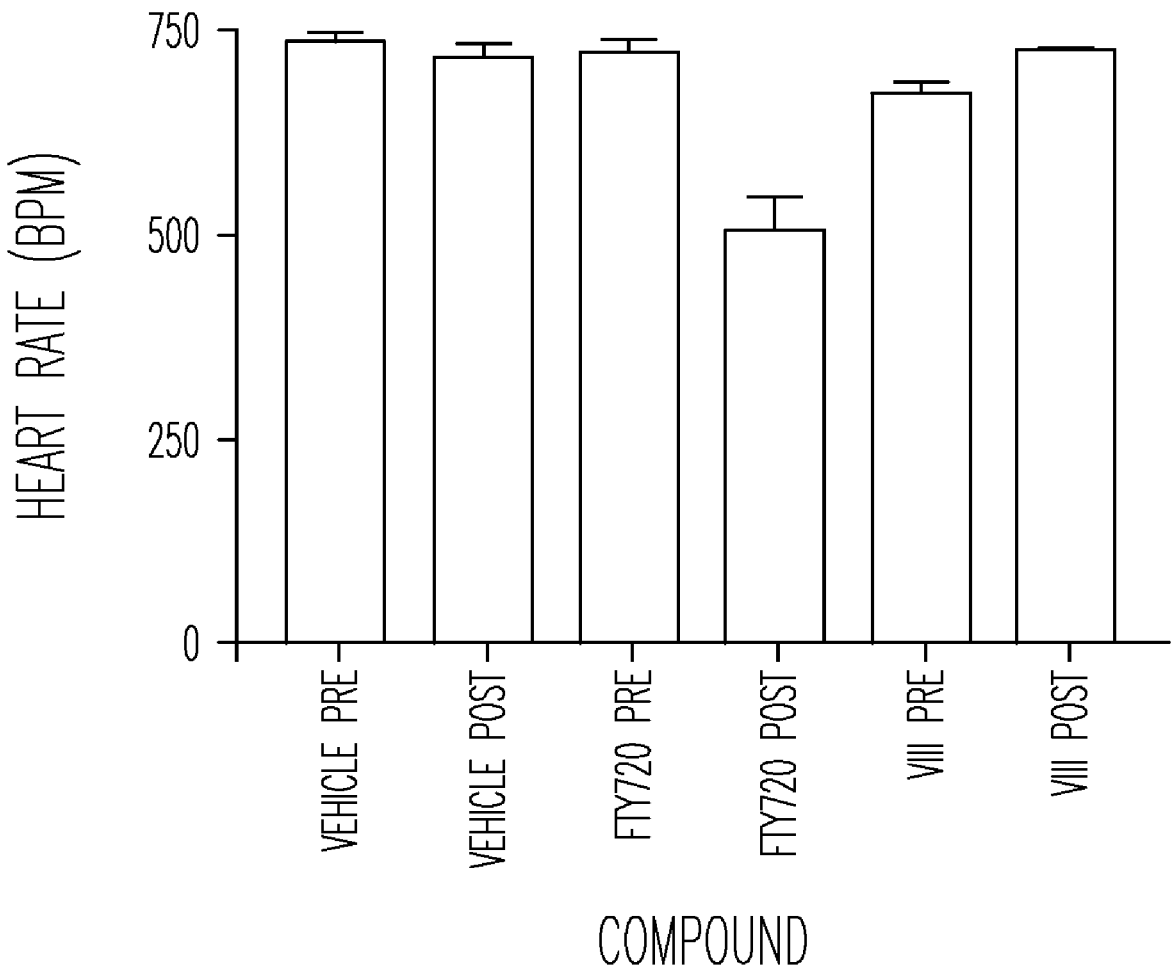
FIG. 11 is a graphical representation of the results of an assay illustrating that compound VIII has no effect on the heart rate of mice. In the assay the test compound was administered via IV Dosing and the vehicle was 2% cyclodextrin.

Mice were dosed with compound VIII, FTY720 (intravenous, 3 mg/kg) or vehicle (2% hydroxypropyl beta-cyclodextrin) and heart rate measured at 1 hour post dosing. Heart rate was captured in unrestrained, conscious animals using the ECGenie™ system. The results are illustrated in FIG. 11.

The invention should not be construed to be limited solely to the assays and methods described herein, but should be construed to include other methods and assays as well. Other methods which were used but not described herein are well known and within the competence of one of ordinary skill in the art of chemistry, biochemistry, molecular biology, and clinical medicine. One of ordinary skill in the art will know that other assays and methods are available to perform the procedures described herein.

The abbreviations used herein have their conventional meaning within the clinical, chemical, and biological arts. In the case of any inconsistencies, the present disclosure, including any definitions therein will prevail.

The disclosures of each and every patent, patent application, and publication cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

We claim:
1. A compound of formula I:

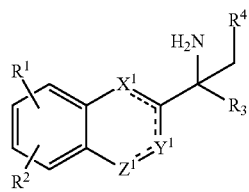

wherein
$X^1$, $Y^1$ and $Z^1$ are independently $CR^a$ and $CR^aR^b$;
$R^1$ is hydrogen, halo, $(C_1-C_{10})$alkyl, $(C_1-C_{10})$haloalkyl, or $(C_1-C_{10})$alkoxy;
$R^2$ is hydrogen, halo, $(C_1-C_{20})$alkyl, $(C_1-C_{20})$alkoxy; $(C_2-C_{26})$alkoxyalkyl; $(C_2-C_{20})$alkenyl, $(C_2-C_{20})$alkynyl, $(C_3-C_{12})$cycloalkyl, $(C_6-C_{10})$aryl, $(C_7-C_{30})$arylalkyl, $(C_2-C_{10})$heterocyclic, and $(C_5-C_{10})$heteroaryl;

----- in $X^1$===C===$Y^1$===$Z^1$ represents one optional double bond; $R^3$ is hydrogen, $(C_1-C_{10})$alkyl, hydroxy$(C_1-C_{10})$alkyl, or $(C_1-C_{10})$alkoxy;
$R^4$ is hydroxyl (—OH), phosphate (—$OPO_3H_2$), phosphonate (—$CH_2PO_3H_2$), halophosphonate, or thiophosphonate;
$R^a$, and $R^b$ are independently hydrogen, or $(C_1-C_{10})$alkyl;
wherein the alkyl groups of $R^1$ are optionally substituted with 1, 2, 3, or 4 substituent groups where the substituent groups independently are halo, $(C_1-C_{10})$alkoxy or cyano;
wherein any of the alkyl, alkenyl, alkynyl, cycloalkyl, aryl, heterocyclic, or heteroaryl groups of $R^2$ are optionally substituted with 1, 2, 3, or 4 substituent groups where the substituent groups independently are $(C_1-C_{10})$alkyl, $(C_1-C_{10})$alkoxy, or $C_6$-aryl; or wherein one or more of the carbon atoms in the $R^2$ alkyl groups can be independently replaced with non-peroxide oxygen; or
a pharmaceutically acceptable salt or ester thereof.

2. The compound of claim 1, wherein $R^1$ is hydrogen, fluorine, chlorine, bromine, trifluoromethyl, methoxy, $(C_1-C_6)$alkyl, $(C_1-C_6)$haloalkyl, $(C_1-C_6)$alkyl substituted with, alkoxy or cyano, alkyl-substituted aryl, aryl-substituted alkyl, or aryl-substituted arylalkyl.

3. The compound of claim 2, wherein $R^1$ is hydrogen, trifluoromethyl, or —$CH_2CF_3$.

4. The compound of claim 2, wherein $R^1$ is benzyl, phenylethyl, or methyl benzyl.

5. The compound of claim 1, wherein $R^2$ comprises —$CH_2$—$CH_2$—O—$CH_2$—$CH_2$—O—.

6. The compound of claim 1, wherein $R^2$ is $(C_1-C_{10})$alkyl, $(C_2-C_{10})$alkenyl and $(C_2-C_{14})$alkynyl, $(C_1-C_{10})$alkoxy or $(C_2-C_{16})$alkoxyalkyl.

7. The compound of claim 6, wherein $R^2$ is $(C_1-C_{10})$alkyl, $(C_1-C_{10})$alkoxy or $(C_2-C_{12})$alkoxyalkyl.

8. The compound of claim 7, wherein $R^2$ is methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.

9. The compound of claim 1, wherein each of $X^1$, $Y^1$ and $Z^1$ is $CH_2$.

10. The compound of claim 1, wherein $R^3$ is hydrogen, methyl, hydroxymethyl, ethyl, hydroxyethyl, propyl, or isopropyl.

11. The compound of claim 10, wherein $R^3$ is hydrogen, methyl, hydroxymethyl, ethyl, or hydroxyethyl.

12. The compound of claim 1, having the formula

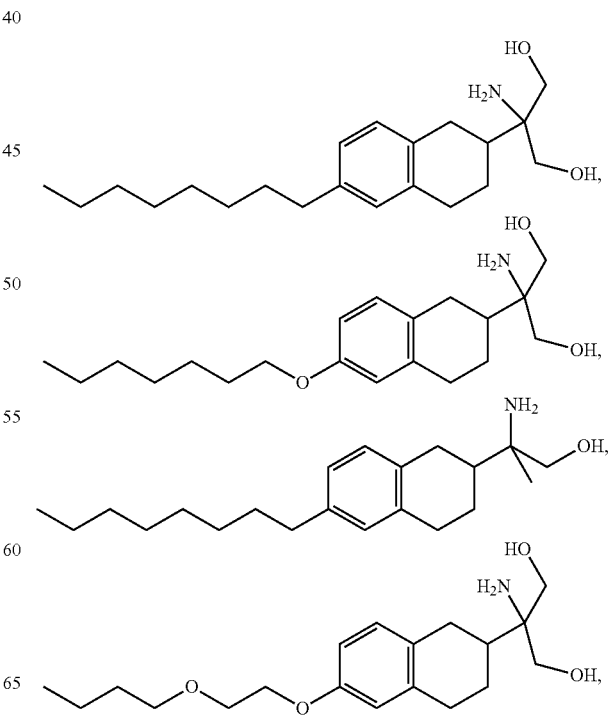

-continued

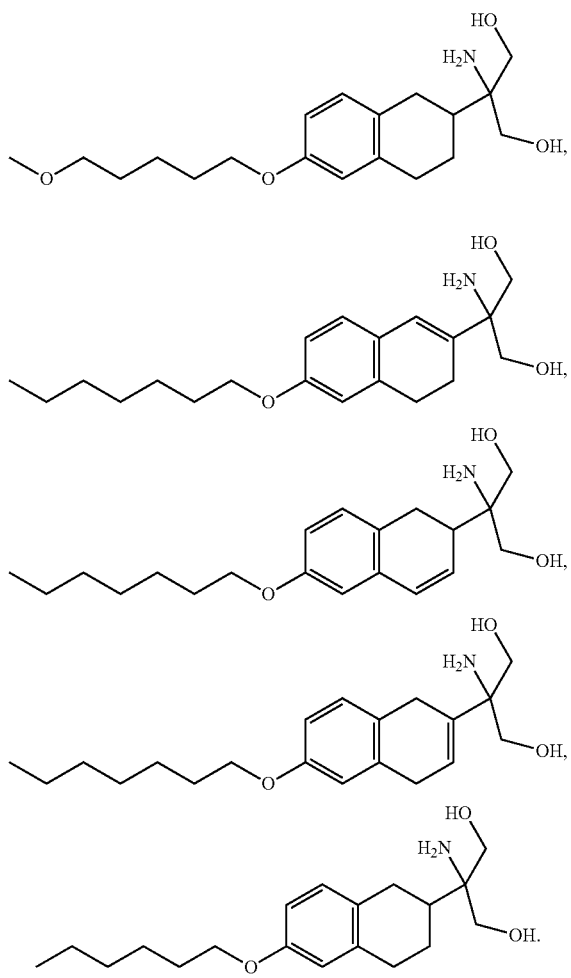

13. The compound of claim 1, having the formula:

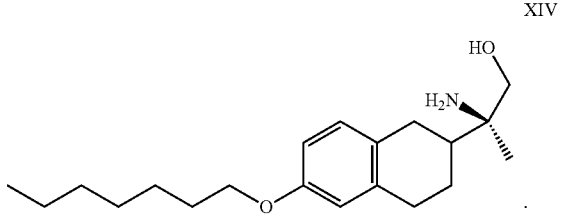

XIV

14. A method for treatment of a pathological condition or symptom in a mammal, wherein the activity of sphingosine 1-phosphate receptors is implicated and agonism of such activity is desired, comprising administering to said mammal an effective amount of a compound of claim 1; and
   wherein the pathological condition or symptom is uveitis, type I diabetes, rheumatoid arthritis, inflammatory bowel diseases, multiple sclerosis, or altering of lymphocyte trafficking.

15. The method of claim 14, wherein the pathological condition or symptom is uveitis, type I diabetes, rheumatoid arthritis, inflammatory bowel diseases, or multiple sclerosis.

16. The method of claim 15, wherein the pathological condition or symptom is multiple sclerosis.

17. The method of claim 14, wherein the treatment of a pathological condition is altering lymphocyte trafficking 18. The method of claim 17, wherein altering lymphocyte trafficking provides prolonged allograft survival.

19. The method of claim 18, wherein the allograft is for transplantation.

20. A method for treatment of a pathological condition or symptom in a mammal, wherein the activity of S1P lyase is implicated and inhibition of the S1P lyase is desired, comprising administering to said mammal an effective amount of a compound of claim 1; and
   wherein the pathological condition or symptom is uveitis, type I diabetes, rheumatoid arthritis, inflammatory bowel diseases, multiple sclerosis, or altering of lymphocyte trafficking.

* * * * *